United States Patent [19]

Treuner

[11] Patent Number: 5,112,968
[45] Date of Patent: May 12, 1992

[54] MONOBACTAM HYDRAZIDE DERIVATIVES

[75] Inventor: Uwe D. Treuner, Etterzhausen, Fed. Rep. of Germany

[73] Assignee: E. R. Squibb & Sons, Inc., Princeton, N.J.

[21] Appl. No.: 386,070

[22] Filed: Jul. 28, 1989

[51] Int. Cl.⁵ .................. C07D 205/00; C07D 491/08
[52] U.S. Cl. ...................................... 540/355; 546/261
[58] Field of Search ................ 540/203, 355; 546/261

[56] References Cited

U.S. PATENT DOCUMENTS

| | | | |
|---|---|---|---|
| 4,587,047 | 5/1986 | Breuer et al. | 540/355 |
| 4,670,553 | 6/1987 | Breuer et al. | 540/363 |
| 4,743,685 | 5/1988 | Breuer et al. | 540/363 |
| 4,772,693 | 9/1988 | Breuer et al. | 540/363 |
| 4,775,670 | 10/1988 | Sykes et al. | 514/210 |
| 4,904,775 | 2/1990 | Sundeen et al. | 540/363 |
| 4,939,253 | 3/1990 | Breuer et al. | 540/363 |
| 4,959,470 | 9/1990 | Treuner | 540/363 |

OTHER PUBLICATIONS

Moritz, DE 2,162,179 Chemical Abstracts vol. 79, 1973 Abs. 106119s.
American Society for Microbiology, Program and Abstracts of the Twenty-Fifth Interscience Conference on Antimicrobial Agents and Chemotherapy, 1985, pp. 158 and 159.
American Society for Microbiology, Program and Abstracts of the Twenty-Fifth Interscience Conference on Antimicrobial Agents and Chemotherapy, 1986, pp. 253 and 254.
Chemical Abstracts, 99, 175469f, 1983.
Abstract No. 646 from 1984 ICAAC meeting. "Antimicrobial Activities of 1-Carbacephem Compounds and their Structure-Activity Relationships", Mochida et al.

Primary Examiner—Mukund J. Shah
Assistant Examiner—E. C. Ward
Attorney, Agent, or Firm—Ellen K. Park

[57] ABSTRACT

Compounds having the formula

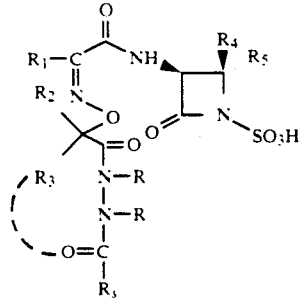

and pharmaceutically acceptable salts thereof which possess antibacterial activity.

$R_1$ is a substituted hydroxy pyridone of the formulae:

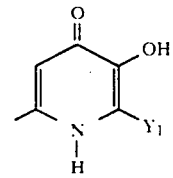

and

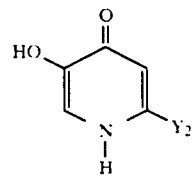

wherein $Y_1$ is $CH_2X$; $COOR_6$; $CONR_7R_8$; OH; $OCH_2R_9$; $CHF_2$; CHO; $CH=N-OR_{10}$; $CH=CH-R_{11}$; CN; $CH=N-NHR_{12}$, and $Y_2$ is hydrogen; COOH; $CONH_2$; CN; $CSNH_2$; COO lower alkyl; $CONR_7/R_8$.

45 Claims, No Drawings

MONOBACTAM HYDRAZIDE DERIVATIVES

BRIEF DESCRIPTION OF THE INVENTION

Compounds having the formula

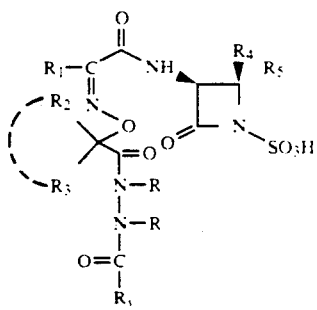

and pharmaceutically acceptable salts thereof which possess antibacterial activity. In formula I, and throughout the specification, the symbols are as defined below:

$R_4$ and $R_5$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_4$ and $R_5$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein X$_1$ is azido, amino (—NH$_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

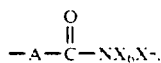

—S—X$_2$, or —O—X$_2$ (wherein A, X$_2$, X$_6$ and X$_7$ are as hereinafter defined)], —S—X$_2$ or —O—X$_2$ wherein X$_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl], and in the case of when X$_1$ is O—X$_2$ then X$_2$ can also be alkylideneamino, alkanoylamino, carboxyalkylideneamino, alkylsulphonylamino, alkoxycarbonylalkylsulphonylamino or N,N-cyclodialkanoylamino,

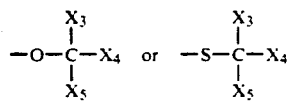

wherein one of X$_3$ and X$_4$ is hydrogen and the other is hydrogen or alkyl, or X$_3$ and X$_4$ when taken together with the carbon atom to which they are attached form a cycloalkyl group; and X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

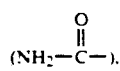

(substituted amino)carbonyl, or cyano (—C≡N)], or

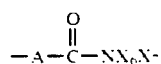

[wherein A is —CH=CH—, —CH$_2$)$_m$—, —CH$_2$)$_m$—O—, —(CH$_2$)$_m$—NH—, or —CH$_2$—S—CH$_2$—, m is 0, 1 or 2, and X$_6$ and X$_7$ are the same or different and each is hydrogen, alkyl, phenyl or substituted phenyl, or X$_6$ is hydrogen and X$_7$ is amino, substituted amino, alkanoylamino or alkoxy, or X$_6$ and X$_7$ when taken together with the nitrogen atom to which they are attached form a 4, 5, 6 or 7-membered heterocycle];

R$_2$ and R$_3$ are the same or different and each is hydrogen or alkyl or R$_2$ and R$_3$ together with the carbon atom o which they are attached are a 3,4,5 or 6-membered cycloalkyl group;

When R$_2$ and R$_3$ are different both optical isomers are included. (R and S)

R is hydrogen or methyl;

R$_5$ is a substituted hydroxy pyridone of the formulae:

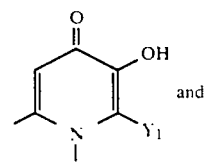

and

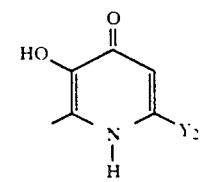

R$_1$ is phenyl, substituted phenyl, a 5 or 6-membered heterocycle containing one or two nitrogen, oxygen or sulfur atoms. These heterocycle groups may be substituted as described previously with the amino group being the preferred substituent. Exemplary heterocyclic groups for R$_1$ are

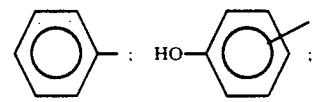

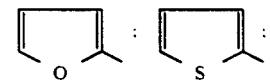

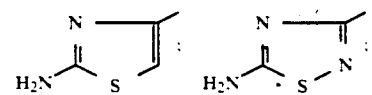

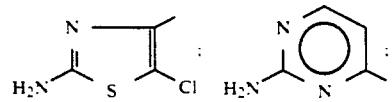

-continued

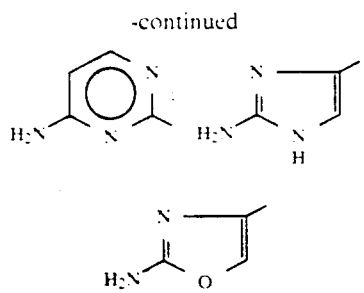

$Y_1$ is $CH_2X$; $COOR_6$; $CONR-R_8$; OH; $OCH_2R_9$; $CHF_2$; CHO; $CH=N-OR_{10}$; $CH=CH-R_{11}$; CN; $CH=N-NHR_{12}$.

X is hydrogen; halogen; $OR_{13}$; $SR_{14}$; $SO_2R_{15}$ $NHR_{16}$; $NR_1 \cdot R_{18}$; $N_3$; CN; SCN; $COOR_{19}$ $CONH_2$; $CSNH_2$; $CH_2R_{20}$.

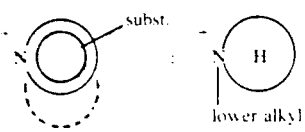

Examples of

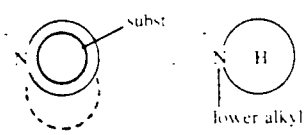

are

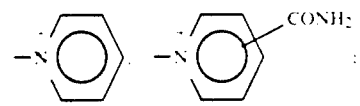

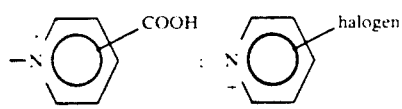

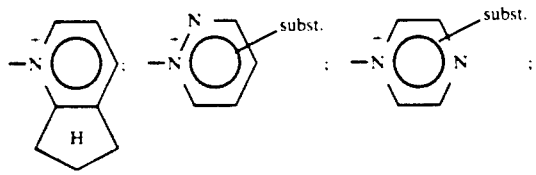

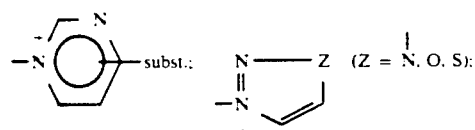

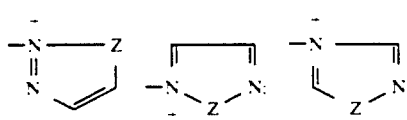

-continued

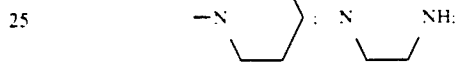

$R_6$ is hydrogen; ion⁻; lower alkyl; substituted lower alkyl; aralkyl $R_7$ and $R_8$ is hydrogen; one of $R_7$ and $R_8$ is hydrogen and the other lower alkyl; substituted lower alkyl; aralkyl; aryl or a 5 or 6 membered heterocycle. $R_7$ and $R_8$ may also be both lower alkyl or part of a saturated heterocycle.

Examples of saturated heterocycles for $R_7$ and $R_8$ are

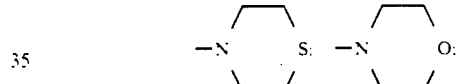

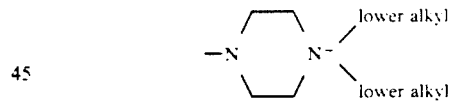

$R_9$ is hydrogen; lower alkyl; aryl; COOH; COO-lower alkyl; $CONH_2$.

$R_{10}$ is hydrogen; lower alkyl.

$R_{11}$ is hydrogen; CN; COOH; COO-lower alkyl; O-lower alkyl; S-lower alkyl; halogen $R_{12}$ is hydrogen; lower alkyl; CO-lower alkyl; aryl; heterocycle; CO-aryl or CO-heterocycle $R_{13}$ is hydrogen; lower alkyl; $CH_2$-COO lower alkyl; $CH_2COOH$; $CONH_2$; $CH_2-CONH_2$;

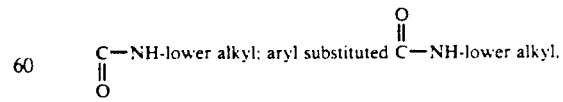

substituted aryl; CO-lower alkyl; CO-aryl (both also substituted).

$R_{14}$ is hydrogen; lower alkyl; $-CH_2COO$-lower alkyl; $CH_2COOH$; $CH_2CONH_2$; heterocycle; substituted heterocycle.

Examples of $R_{14}$ groups are $CH_3$; $CH_2COOCH_3$;

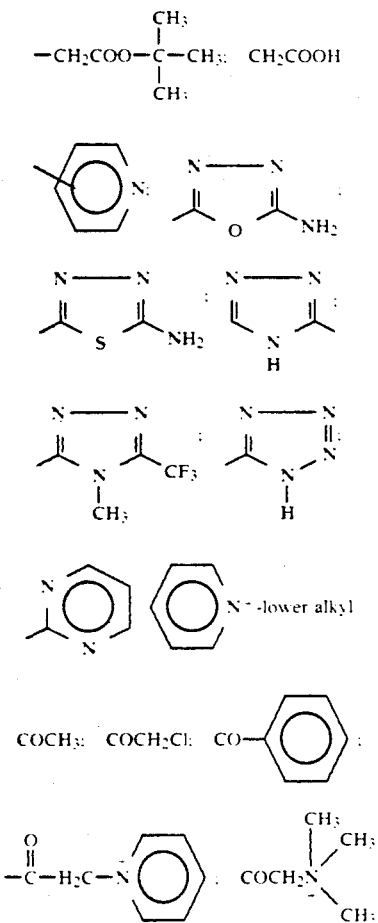

$R_{15}$ is hydrogen; lower alkyl; CH$_2$COO-lower alkyl; COOH; CONH$_2$.

$R_{16}$ is hydrogen; lower alkyl; CONH$_2$; CONH-lower alkyl; CONH-aryl; CONH substituted lower alkyl; CH=NH; C—NH$_2$;

$$-\overset{NH}{\underset{N-(CH_2)_nCH_3}{C-NH_2}} \quad ; CSNH_2;$$

CSNH lower alkyl; CSNH aryl; CSNH-heterocycle; n=1-3; CH$_2$—COOH (lower alkyl); CH$_2$CH$_2$NH$_2$; CH$_2$—CH$_2$NH—CO lower alkyl.

$R_{17}$ and $R_{18}$ is hydrogen and the other lower alkyl or both together as a part of a saturated heterocycle, e.g.

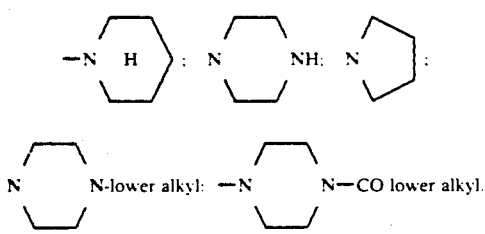

$R_{19}$ is hydrogen; lower alkyl
$R_{20}$ is hydrogen; COOH; COO lower alkyl; CN; OH.
$Y_2$ is hydrogen; COOH; CONH$_2$; CN; CSNH$_2$; COO lower alkyl; CONR$_7$/R$_8$.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having to 10 carbon atoms are preferred.

The term "cycloalkyl" refers to cycloalkyl groups having 3,4,5,6 or 7 carbon atoms.

The term "substituted alkyl" refers to alkyl groups substituted with one or more (preferably 1, 2 or 3), azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_a$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The term "substituted alkanoyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6, or 7-membered heterocycle" (referred to as "R$_c$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl or 1 to 4 carbons, alkoxy of 1 to 4 carbons, alkylsulfonyl, phenyl, substituted phenyl, 2-furfurylideneamino $$\left(\underset{}{\overset{O}{\bigsqcup}} \underset{}{\overset{CH=N-}{}}\right).$$

benzylideneamino and substituted alkyl groups (wherein the alkyl group has 1 to 4 carbons . One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetidinyl, 2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-diozo-1-piperazinyl.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino (—NH$_2$).

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-gluccamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. Of particular interest is the good activity against gram negative organisms in vitro and in vivo exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The intermediate acids and hydrazides of compounds II and III are used to synthesize compounds I of this invention. These intermediates are represented by the following formulae

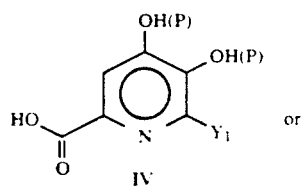
IV or

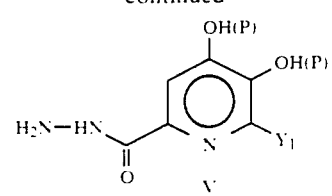
V

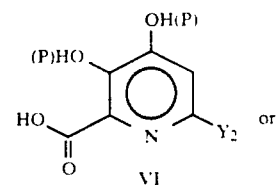
VI or

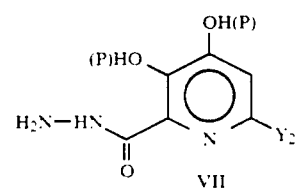
VII wherein P is a protecting group. Compound IV may be converted into formula IVa

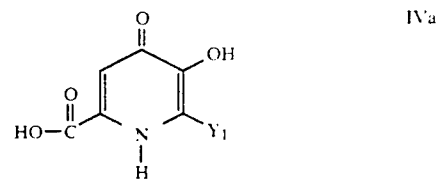
IVa by using standard deprotecting procedures. Compound VI may be converted into formula VIa

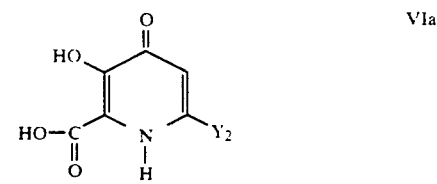
VIa by using standard deprotecting procedures.

Compounds IV and IVa are prepared by reacting maltol with sodium methoxide and benzyl bromide to obtain the compound having the formula

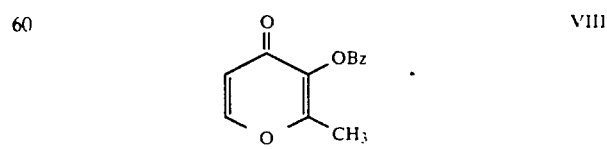
VIII wherein Bz is benzyl. Compound VIII is reacted with ammonia in ethyl alcohol to yield

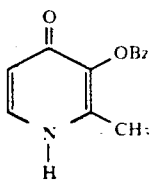

Compound IX is reacted with benzylhalides in the presence of a base such as potassium carbonate or cesium carbonate in a solvent such as methanol, ethanol, or isopropanol at room temperature up to 80° C. to yield the compound of the formula

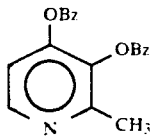

Better yields of compound X are obtained by reacting compound IX with benzyl alcohol, triphenylphosphine and diethyl azodicarboxylate in solvents such as tetrahydrofuran (THF) or dioxane. Compound X is reacted with a peracid such as meta-chloroperbenzoic acid (MCPBA) in solvents such as CHCl$_3$ or dichloromethane to yield the compound of the formula

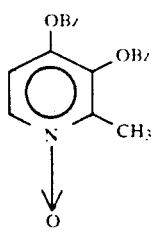

Compound XI is heated with acetic anhydride to yield the compound having the formula

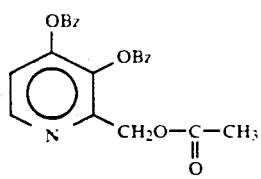

Compound XII is reacted with MCPBA in chloroform or CH$_2$Cl$_2$ at room temperature to about 80° C. to yield the compound having the formula

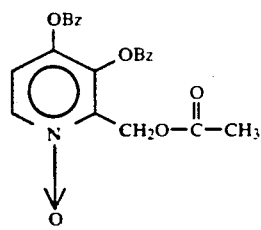

Compound XIII is reacted with dimethylsulfate in acetonitrile at reflux temperature and the intermediate methoxy-2[(acetyloxy)methyl]-3,4-bis(phenylmethoxy) pyridinium monomethylsulfate is isolated and then reacted with potassium cyanide in THF/C$_2$H$_5$OH/H$_2$O at −10° C. to −5° C. to yield the compound having the formula

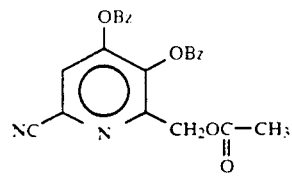

An alternate synthesis of compound XIV is to react compound XIII with dimethylcarbamide chloride in acetonitrile and isolating the intermediate 1-(dimethylaminocarbonyloxy)-2-[(acetyloxy)methyl],3,4-bis(phenylmethoxy) pyridinium chloride and reacting this intermediate with trimethylsilylcyanide and triethylamine in acetonitrile at an elevated temperature to yield compounds of formula XIV. Another alternate synthesis is reacting a compound of the formula XIII with trimethylsilylcyanide and triethylamine in a solvent like acetonitrile or CH$_2$Cl$_2$ at reflux temperature. Saponification of the compounds of formula XIV with a large excess of lithium hydroxide at the reflux temperature in solvent mixtures such as H$_2$O/THF or water/dioxane forms compound XV after acidification.

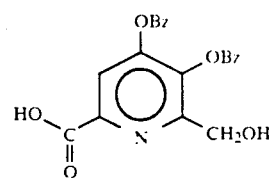

Compound XI can be converted to compound XVI

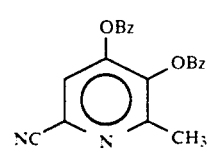

under similar conditions used to transform compound XIII to compound XIV. Saponifications of compound XVI with bases such as KOH, NaOH or preferred LiOH in mixtures of THF/water or dioxane/water and acidification yields a compound having the formula

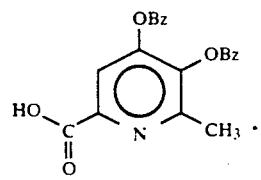

Compound XVII can be reacted with methanol/HCl gas at room temperature to yield the methyl ester having the formula

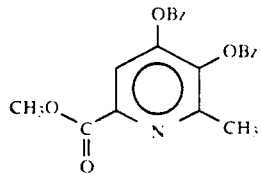

XVII

Compound XVIII can also be obtained from compound XVII when it is reacted with methanol/HCl. Compound XVIII is reacted with MCPBA in chloroform at room temperature to yield the compound having the formula

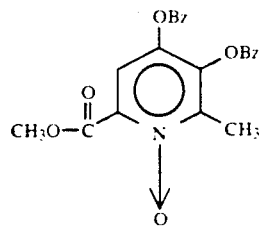

XIX

Heating of compound XIX with excess acetic anhydride yields a compound having the formula

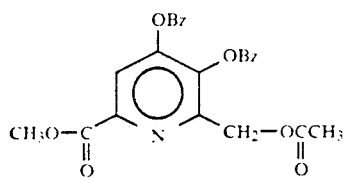

XX

Saponification of compound XX with bases such as KOH, NaOH or LiOH in water/THF or water/dioxane at the reflux temperature results in the salt of compound XV which is then acidified to yield compound XV.

Compound XV can be converted to the intermediates of formula IV by first protecting the carboxylic group and then reacting with known functional groups to result in compounds of IV wherein $Y_1$ is $CH_2OR_{13}$. For example, the protected form of compound XV can be reacted with isocyanates to yield compounds of IV'a wherein $Y_1$ is

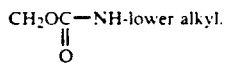

Alkylation of the protected form of XV with alkyl halogenides and bases yields compounds of IV wherein Y is $CH_2O$-lower alkyl and P is benzyl.

Compound XV can be reacted with benzyl bromide or benzyl chloride in dimethylformamide and one equivalent of base such as potassium carbonate or triethylamine at room temperature to form compounds having the formula

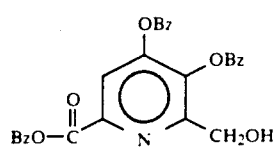

XXI

Compound XV can be reacted with thionylchloride to give a compound having the formula

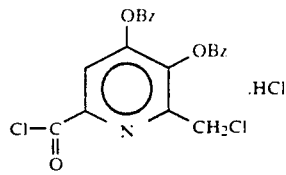

XXII

Compound XXII can be allowed to stand in anhydrous methanol for 24 hours to give a compound of the formula

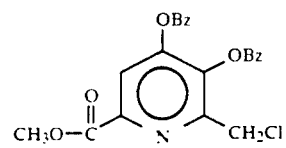

XXIII

Compound XXIII can be reacted with a source of azide ion ($N_3^-$) in DMF in the presence of catalytic amounts of potassium iodide to form a compound having the formula

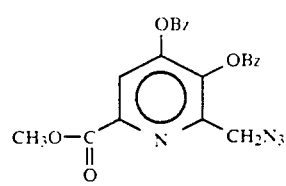

XXIV

Saponification of compound XXIV with potassium hydroxide in mixtures of water with organic solvents such as ethanol, THF, dioxane, methanol at room temperature, followed by acidification gives a compound having the formula

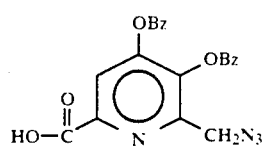

XXV

Using conventional methods for reducing azides such as triethylamine/$H_2S$ gives the compound having the formula

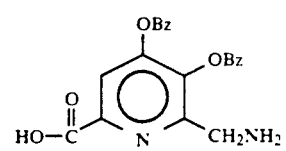

XXVI

Compound XXVI or the carboxylic group protected derivative of XXVI can be converted to the intermediates of IV wherein $Y_1$ is $CH_2$—NH—$R_{16}$ wherein P is benzyl.

For example, compound XXVI can be heated with potassium isocyanate or isothiocyanate, in water/dioxane to yield the intermediate IV wherein $Y_1$ is

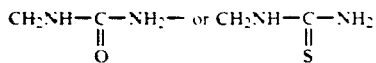

or a protected form of compound XXVI (COOP) can be reacted with isocyantes or isothiocyantes to novel intermediates IVa wherein $Y_1$ is

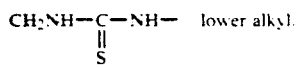

Compound XXIII can be reacted with nucleophiles in solvents such as DMF and dimethylacetamide to form compounds of formula IV wherein $Y_1$ is $CH_2-C\equiv N$, $CH_2-(S)-R_{14}$, $CH_2(O)-R_{13}$ and $CH_2-S-C\equiv N$. Further transformation of a compound of formula IV wherein Y is $C\equiv N$ will yield compounds of formula IVa wherein $Y_4$ is $CH_2COOR_{19}$ and $CONHR_{16}$.

Compound XXI can be oxidized for example with activated manganese oxide in $CH_2Cl_2$ to yield a compound of the formula

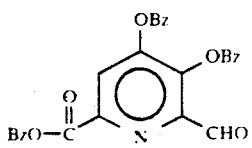

XXVII

Transformation of compound XXVII by conventional procedures produces compounds of formula IVa wherein $Y_1$ is $CH=NO$—lower alkyl, $C\equiv N$, $CONH_2$, $CHF_2$, $CH=CHR_{11}$, $CSNH_2$. Specifically, compound XXVII can be reacted with hydroxylamine or a protected hydroxylamine to give an intermediate with Y being $CH=NOH$. This intermediate can be dehydrated to a compound of formula IV with $Y_1$ being $C\equiv N$. Compound XXVII can be reacted with diethylamino sulfuryltrifluoride in $CH_2Cl_2$ to give a compound of formula IV where $Y_1$ is $CHF_2$. Reaction of compound XXVII with Wittig reagents gives compounds of IV wherein Y is $CH=CHR_{11}$.

Compound XXVII can be oxidized with tetrabutylammonium permaganate in pyridine to give a compound of the formula

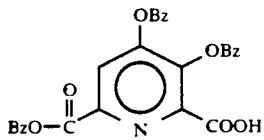

XXVIII

Compound XXVIII can be reacted with dicyclohexylcarbodiimide and 4-pyrollidino-pyridine and t-butanol to give a compound of the formula

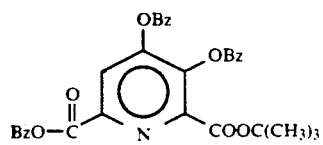

XXIX

Saponification of XXIX with KOH in THF and water gives a compound having the formula

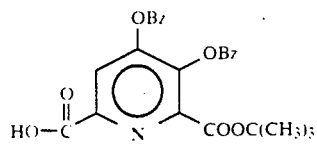

XXX

Compound XXIII can be reacted with pyridines in DMF in the presence of catalytic amounts of potassium iodide to form compounds of IV wherein Y is

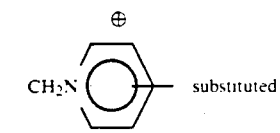

as a salt or a zwitterion.

An alternate procedure to the novel intermediates of IV and IVa is to react O-benzylcomenamic acid with excess benzylbromide in DMF at an elevated temperature to give the fully protected pyridine having the formula

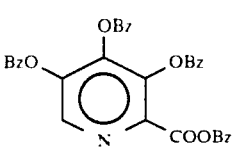

XXXI

Oxidation of compound XXXI with MCPBA in chloroform yields the compound having the formula

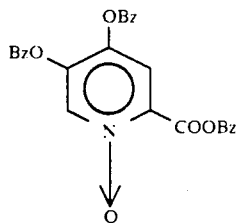

XXXII

Compound XXXII can be first reacted with dimethylsulfate in acetonitrile at reflux temperature, isolating the O-methylpyridinium intermediate and reacting this intermediate with KCN in THF/ethanol to form a compound of the formula

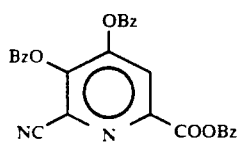

XXXIII

Alternatively, compound XXXIII can be prepared by reacting compound XXXII with dimethylaminocarbonylchloride, followed by trimethylsilylcyanide or by reacting compound XXXII with trimethylsilylcyanide and triethylamine under reflux.

Compound XXXIII can be converted to novel intermediate IVa wherein $Y_1$ is CN, COOH, $COOR_6$.

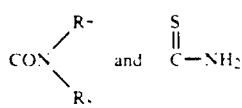

by the methods described above involving compound XXVII.

Compound XXXII can be heated with acetic anhydride to form a compound having the formula

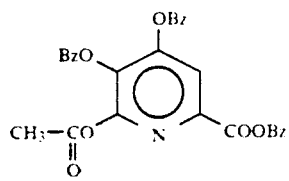

XXXIV

Selective saponification of compound XXXIV with excess ammonium acetate in dioxane/water gives a compound having the formula

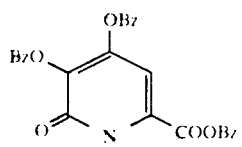

XXXV

Alkylation of compound XXXXV with diazoalkanes in ethanol or with alkylhalides or alkylsulfates and bases such as cesium carbonate yields compounds after saponification having the formula

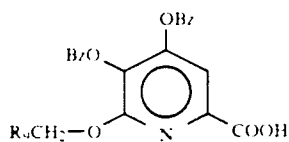

XXXVI

Compounds VI and VIa are prepared by following the procedure described above to obtain compound XII.

Compound XII is saponified with a base such as potassium or sodium hydroxide to yield the compound having the formula

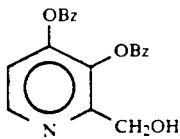

XXXVII

Oxidation of compound XXXVII with manganese dioxide in solvents such as acetone, methanol or methylene chloride results in a compound having the formula

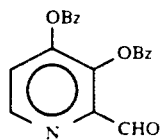

XXXVIII

Further oxidation of compound XXXVIII with silver oxide yields a compound having the formula

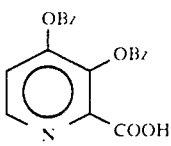

XXXIX

Alternatively, pyromecomic acid can be transformed according to the procedures described in Belgium Patent 625,114 (1963) and J. Org. Chem. 45, 1109 (1980) to compounds having the formula

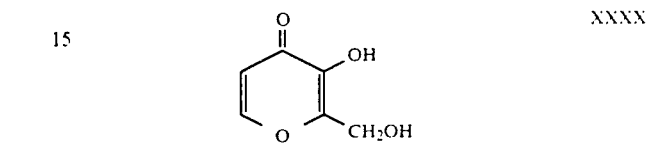

XXXX

Compound XXX can be further converted to a compound having the formula

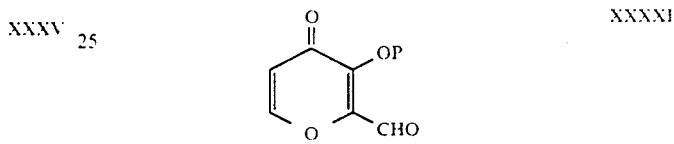

XXXXI and then to compounds having the formula

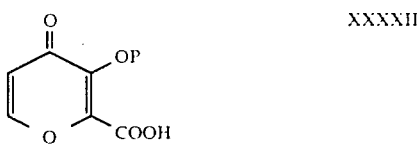

XXXXII following the procedures in J. Heterocyclic Chem. 23, 225 (1986).

Aminolysis of compound XXXXII or protected forms thereof yields compounds of formula

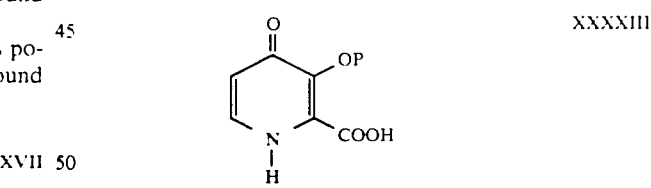

XXXXIII or protected forms thereof.

The hydrazides of formulae V and VII may be prepared from the acids of formulae IV and VI or from the esters of the compounds represented by formulae IV and VI. The hydrazides are prepared by standard procedures which can be represented by the following flow chart:

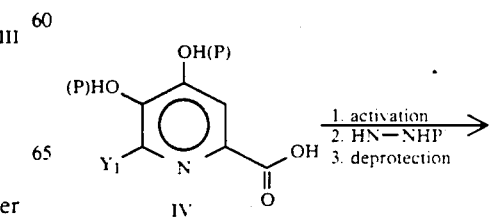

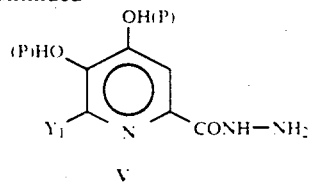

V

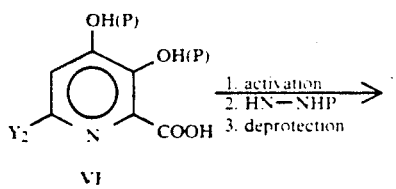

VI 1. activation
2. HN—NHP
3. deprotection

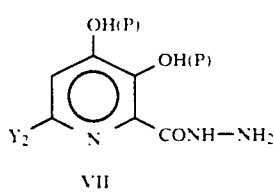

VII wherein P¹ is a protecting group different or the same as P.

The compounds of formula I wherein R is hydrogen may be prepared by the methods outlined in the flow chart described below:

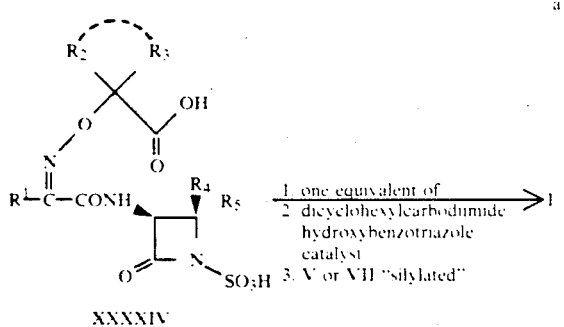

XXXXIV 1. one equivalent of
2. dicyclohexylcarbodiimide hydroxybenzotriazole catalyst
3. V or VII "silylated"
→ I

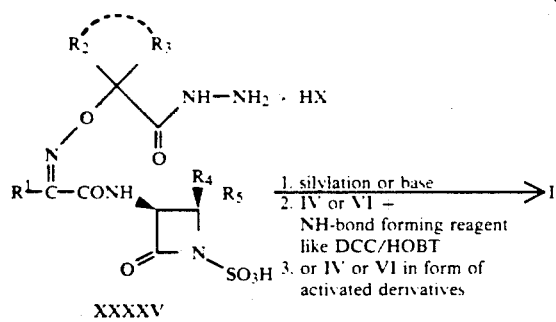

XXXXV 1. silylation or base
2. IV or VI —
   NH-bond forming reagent like DCC/HOBT
3. or IV or VI in form of activated derivatives
→ I

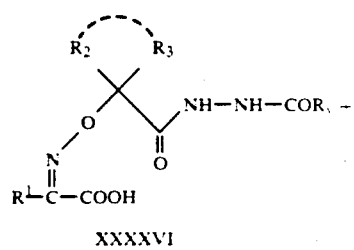

XXXXVI

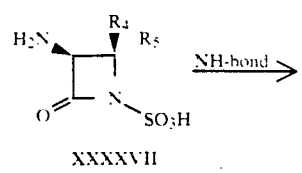

XXXXVII

NH-bond →

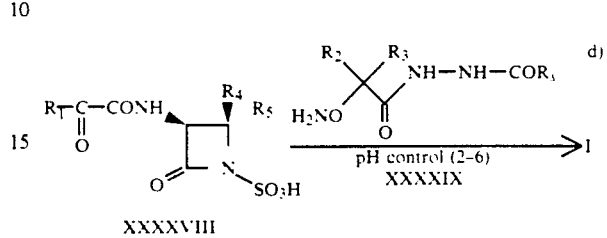

XXXXVIII $+$ $$H_2NO\underset{O}{\overset{R_2\phantom{XX}R_3}{C}}\underset{\phantom{X}}{C}-CONH-NH-COR_1$$

XXXXIX pH control (2-6)
→ I d)

The $Y_1$ and $Y_2$ groups in compound I may be modified by standard procedures for functional group transformation. Compound XXXXIX can be synthesized from protected hydroxylamine derivatives as described below:

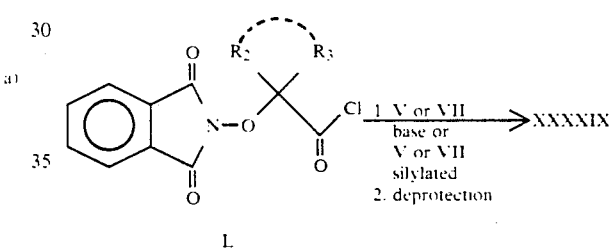

L

1. V or VII
   base or
   V or VII
   silylated
2. deprotection
→ XXXXIX

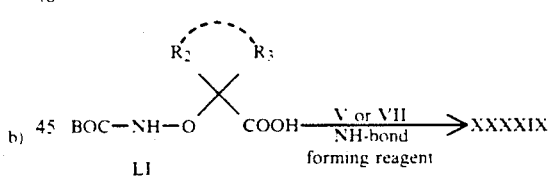

LI

V or VII
NH-bond forming reagent
→ XXXXIX b)

Compounds of formula I wherein R is methyl can be synthesized by the procedure described in the flow chart below:

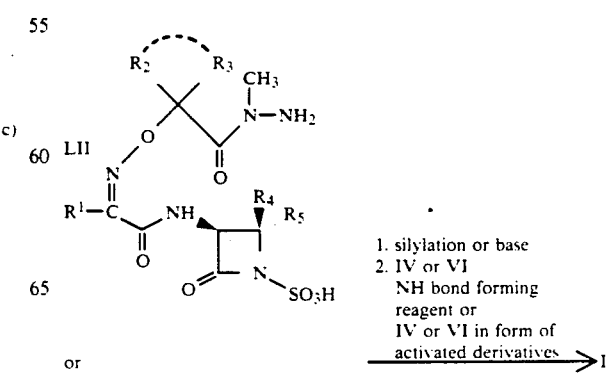

LII 1. silylation or base
2. IV or VI
   NH bond forming reagent or
   IV or VI in form of activated derivatives
→ I c)

or

-continued

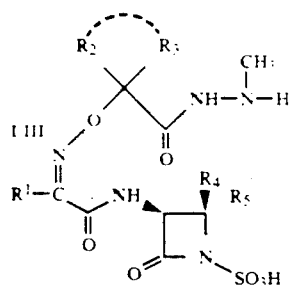

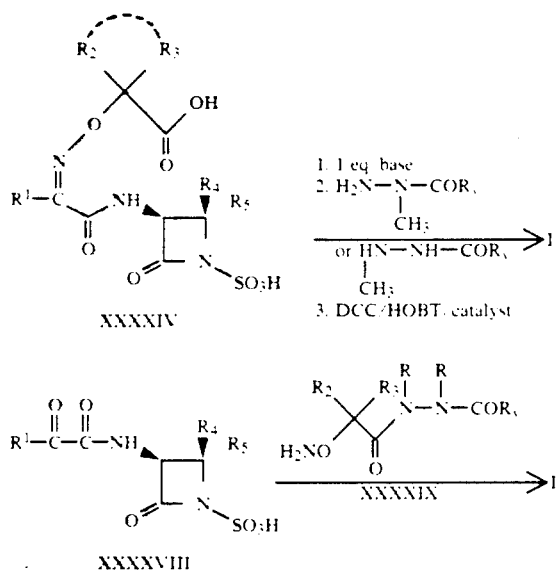

The following examples are specific embodiments of this invention.

EXAMPLE 1

2-Methyl-3-(phenylmethoxy)-4H-pyran-4-one 11.5 g of sodium were dissolved in 300 ml $CH_3OH$ and 63g of maltol were added and stirred at room temperature for one hour. 200 ml $CH_3OH$ were added and then 102 g benzylbromide were dropped in (30 minutes). Refluxing for 3 hours and distilling off the $CH_3OH$ then yielded a residue which was dissolved in 300 ml $H_2O$/300 ml ethyl acetate. The organic phase was washed with water and evaporated. The remaining oil was distilled in vacuo. B.P. (43 mm) = 148°-150° C., 81.5 g colorless oil of the title compound was isolated.

EXAMPLE 2

2-Methyl-3-(phenylmethoxy)-4(1H)-pyridone 62 g of product of Example 1 were dissolved in 300 ml $C_2H_5OH$ containing 18 g $NH_3$. The solution was kept at 110° C. for 16 hours in a glass autoclave. After cooling, the $C_2H_5OH$ was distilled off and the crystalline residue filtered off and washed with 50 ml $C_2H_5OH$ at 0° C.; 49.7g beige crystals were recovered M.P. = 162° C.

EXAMPLE 3

2-Methyl-3,4-bis(phenylmelthoxy)pyridine

EXAMPLE 3a 1-(phenylmethyl)-2-methyl-3-(phenylmethoxy) 4-pyridone 73 g of the product of Example 2 were dissolved in 4 liters of ethanol (dry), 25 g $K_2CO_3$ powderized and 70 g benzylbromide were added. After refluxing for 4 hours and filtration, the solvent was distilled off and the residue extracted with 4 liters of hot petroleum ether in 3 parts. After cooling to room temperature and filtration the petroleum ether filtrate was concentrated to 2 liters and cooled to $-10°$ C. 31 g of white crystals of the title compound of Example 3 were obtained. The formed title compound 3A was insoluble in petroleum ether at room temperature white crystals. 70% of total yield.

EXAMPLE 3b 2-methyl-3,4.bis(phenylmethoxy)pyridine (alternative synthesis)

To 154.8 g of the product of Example 2, 86.4 g benzylalcohol and 210 g triphenylphosphine suspended in 1.5 liters (dry) tetrahydrofurane was added a solution of 139.2g diethylazodicarboxylate in 500 ml tetrahydrofuran within 20 minutes. The temperature rose to 53° C. for several hours. After 4.5 hours a clear solution was obtained. After standing overnight, a solution of HCl in ether (28 g) was added. Hydrochlorides of Example 3 and 3 A crystallized from the solution. After cooling they were isolated by filtration and washed with ether and petroleum ether. 230g of the mixture of HCL salts of 3 and 3A was suspended in 2 liters of ethyl acetate and 1 liter of water. The pH was adjusted to 7.0 with concentrated NaOH solution. The organic phase and two organic was phases were combined and dried over $Na_2SO_4$. Filtration and distilling off the solvent yielded an oily residue which was passed through a column with 600 g $SiO_2$. Ethylacetate as eluent. Only the title compound of Example 3B, 151.8 g, was eluted from the column. Eluation of 3A is possible with $CH_3OH$. M.P.=92° C. (title comp. 3)

EXAMPLE 4

2-Methyl-3,4-bis(phenylmethoxy)pyridine, 1-oxide 102 g of the compound of Example 3B were dissolved in 200 ml $CHCl_3$ and 67.5 g metachloroperbenzoic acid were added in three parts while stirring. The solution was kept for three hours at 50° C. then at 10 hours at room temperature. The precipitate of metachlorobenzoic acid was filtered off and the filtrate evaporated. The residue was dissolved in 300 ml ethyl acetate and extracted 3 times with $Na_2CO_3$ solution ($H_2O$) each 50 ml. Finally the organic phase was washed with water and dried over $Na_2CO_4$. The ethyl acetate was distilled off and the solid residue recrystallized from $CH_3OH$/water, 92.5 g of the title compound as white crystals was isolated. M.P. = 106° C.

EXAMPLE 5

3,4-Bis(phenylmethoxy)-2-pyridinemethanol, acetate ester 3.22 g of the compound of Example 4 and 20 ml acetic anhydride ($AC_2O$) were heated for one hour at 90°-100° C. Excess acetic anhydride and formed acetic acid were distilled off and the residue dissolved in 50 ml ethyl acetate and 50 ml ice water. NaHCO₃ was added and the mixture stirred for 30 minutes. The organic layer was separated then, washed with water and dried over Na₂SO₄. Evaporation yielded 3.24 g of the title compound. Recrystallization from CCl₄. M.P. = 39 −47° C.

EXAMPLE 6

3,4-Bisiphenylmethoxy]-2-pyridinemethanol, acetate ester, 1-oxide 56 g of the compound from Example 5 were dissolved in 250 ml CHCl₃ and 34 g metachloroperbenzoic acid were added. The temperature of the solution warmed up to 45° C. for 30 minutes. Then it was heated to 60° C. for 1 hour and then cooled to 0° C. for 1 hour. The precipitated metachlorobenzoic acid was filtered off and washed with 50 ml cold CHCl₃. The filtrate was extracted with NaHCO₃ solution (ice cold). Evaporation of the organic phase yielded an oily residue. This was stirred with 100 ml cold ether. 37.3 g white crystals of the title compound were obtained. M.P. = 99° C.

EXAMPLE 7

6-[(Acetyloxy)methyl]-4,5-bis(phenylmethoxy)-2-pyridinecarbonitrile 36 g of the title compound of Example 6 and 12 g dimethylsulfate were refluxed for 2 hours in 300 ml CH₃CN and then stirred for 18 hours at room temperature. The solvent was distilled off then and the oily residue containing 1-methoxy-3,4-bis(phenylmethoxy)-2-[(acetyloxy)-methyl]pyridinium monomethylsulfate was dissolved in 300 ml tetrahydrofuran /C₂H₅OH (8:2) and at 0° C. 6 g KCN in 40 ml H₂O were added dropwise. After 1 additional hour of stirring and the solution was evaporated (vacuo, <40° C.) and the residue dissolved in 100 ml ethyl acetate and extracted 3 times with each 50 ml of water. The dried organic phase was evaporated again and yielded a brown oil. This was dissolved in 500 ml ether, filtered and stirred with 10 g active carbon. The filtrate was cooled down then to −50° C. 12.4 g crystals of the title compound (white) were obtained after one hour. Filtration and washing with petroleum ether followed. Recrystallization yielded 10.1 g. M.P. = 92°-93° C.

EXAMPLE 7a

2-[(Acetyloxy)methyl]-1-[[(dimethylamino)carbonyl]oxy]-3,4-bis(phenylmethoxy) pyridinium chloride To 3.80 g of the title compound of Example 6, dissolved in acetonitrile, were added 1.08 g dimethylcarbamidchloride. After two hours ether was added and the crystals of the title compound were isolated by filtration. M.P. 108°-109° C.

EXAMPLE 7b

6-[(Acetyloxy)methyl]-4,5-bis(phenylmethoxy)-pyridinecarbonitrile

To 7 g of the title compound of Example 6, dissolved in 50 ml acetonitrile, were added 2.0 g dimethylcarbamidchloride. After stirring, crystals from Example 7A were formed. Without isolation 2.2 g trimethylsilylcyanide were added. After a short time a clear solution was obtained. Stirring was continued for 24 hours at room temperature. The solvent was distilled off then, and the residue stirred for 30 minutes with brine and ethyl acetate. The isolated organic phase was washed with water and dried. Evaporation gave an oil of crude title compound. This was purified by column chromatography on SiO₂, ethyl acetate/cyclohexane (6:4) as eluents. The fraction containing the title compound was collected and the solvents distilled off. The residue was dissolved in ether and cooled to −30° C. White crystals of the title compound, 3.01 1g, were obtained. M.P. 98°-99° C.

EXAMPLE 8

6-(Hydroxymethyl)-4,5-bisiphenylmethoxy)-2-pyridinecarboxylic acid 37 g of the title compound of Example 7 and 81.5 g lithiumhydroxy hydrate in 300 ml dioxane and 200 ml H₂O were refluxed for 60 hours. The dioxane/water was distilled off and the residue suspended in 200 ml cold water, stirred for 10 minutes and filtered off, washed with 50 ml ice water two times. The filter residue, white crystals, is the Li-salt of the compound of Example 8 which is very insoluble in water. It was suspended in 500 ml tetrahydrofurane and the pH was adjusted to 1.0 with concentrated HCl and a clear solution was formed. 500 ml H₂O were added and the title compound crystallized from the solution. 32.3 g after drying over P₂O₅. M.P. = 197° C.

EXAMPLE 9

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid,
2-[[1,4-dihydro-5-hydroxy-6-(hydroxymethyl)]-4-oxo-2-pyridinyl]carbonyl]-hydrazide, monopotassium salt

EXAMPLE 9a 6-(Hydroxymethyl)-4,5-bisiphenylmethoxy)-2-pyridinecarboxylic acid,
2-[(1,1-dimethylethoxy)carbonyl]hydrazide 5.1 g of Example 8, 1.8 g BOC-hydrazide and 2.1 g hydroxybenzotriazole were dissolved in 100 ml dimethylformamide. A solution of 3 g dicyclohexylcarbodiimide (DCC) in 25 ml dimethylformamide was added dropwise while stirring continued at room temperature. After stirring continuously overnight and filtration, the dimethylformamide of the filtrate was distilled off in vacuo. The residue was dissolved in ethylacetate and washed with NaHCO₃-solution and brine. The dried organic phase was evaporated then, and the residue stirred with petrol ether yielding the title compound of Example 9A. M.P. 158° C.

EXAMPLE 9b 1,4-Dihydro-5-hydroxy-6-(hydroxymethyl)-4-oxo-2-pyridinecarboxylic acid,
2-[(1,1-dimethylethoxy)carbonyl]hydrazide To 6.5 g of the compound of Example 9A dissolved in 150 ml CH₃OH were added 3 g Pd/C(10%), and a stream of H₂ was bubbled through the reaction mixture for 1 hour. The catalyst was filtered off and the solvent distilled off. The residue was stirred with petrolether. Yield: 4.1 g of the title compound of Example 9B beige powder. M.P. 174° C. (dec.)

EXAMPLE 9c 1,4-Dihydro-5-hydroxy-6-(hydroxymethyl)-4-oxo-2-pyridinecarboxylic acid, hydrazide, trifluoroacetate (1:1) salt 4.0 g of the compound of Example 9B and 30 ml trifluoroacetic acid were stirred for 30 minutes at room temperature. With cooling 200 ml ether were added. The obtained precipitate was the title compound of Example 9C. 3 g. M.P. 224° C.

EXAMPLE 9d

[2S-[2α,3β(Z)]]-2-[[[1-(2-Amino-4-thiazolyl)-2-[(2-methyl-4-oxo
-1-sulfo-3-azetidinyl)amino-2-oxoethylidene]amino]oxy]-2-methylpropanoic acid,
2-[[1,4-dihydro-5-hydroxy-6 TM (hydroxymethyl)-4-oxo-2-pyridinyl]carbonyl]-hydrazide, monopotassium salt 4.36 g Aztreonam zwitterion, 2.3 ml tributylamine. 0.01 g 4-dimethylaminopyridine, 1.5 g N-hydroxybenzotriazole and 2.2 g dicyclohexylcarbodiimide were stirred in 50 ml dimethylformamide for one hour. Then a solution, obtained from stirring 3 g of the title compound of Example 9C in 50 ml acetonitrile and 11 ml MSTFA for one hour, evaporation and redissolving the oily residue in 20 ml dimethylformamide, was added. After stirring overnight and filtration, the dimethylformamide of the filtrate was distilled off. The residue was dissolved in acetone, filtered again and a solution of 6.0 g perfluorobutanesulfonic acid potassium salt in acetone was added. A precipitate of 5.1 g of crude title compound was obtained. 2 g of this were purified by column chromatography. M.P. 300° C. (dec.)

EXAMPLE 10

[2S-2α,3β(Z)]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid,
2-[(1,4-dihydro-5-hydroxy-6-methoxy-4-oxo-2-pyridinyl)carbonyl]hydrazide, monopotassium salt.

EXAMPLE 10a

6-Methoxy-4,5-bis(phenylmethoxy)-2-pyridine-carboxylic acid,
2-[(1,1-dimethylethoxy)carbonyl]hydrazide.

3.6 g 6-methoxy-4,5-bis(phenylmethoxy)-2-pyridinecarboxylic acid and 0.1 g N-hydroxybenzotriazole; 0.01 g 4-dimethylaminopyridine and 2.1 g dicyclohexylcarbodiimide were dissolved in 100 ml THF. After stirring for ½ hour at room temperature 1.32 g t-butyloxycarbonyl hydrazide was added and stirring continued over night. The formed dicyclohexylurea was filtered off and the filtrate was evaporated. The residue was dissolved in 50 ml ethylacetate and washed with NaHCO₃ solution and water. After drying over Na₂SO₄ the ethylacetate was distilled off. 3 g of the title compound as a white solid were obtained.

EXAMPLE 10b 1,4-Dihydro-5-hydroxy-6-methoxy-4-oxo-2-pyridinecarboxylic acid, hydrazide, trifluoroacetate (1:1) salt.

3 g of the compound of Example 10A were dissolved in 80 ml methanol, and 0.5 g Pd/C (10%) were added. A stream of Hz was bubbled through &he reaction suspension for 1 hour. The catalyst was filtered off then, washed with methanol, and the filtrate evaporated. The oily residue was 1.8 g. (crude). This material was stirred with 20 ml trifluoroacetic acid for 30 minutes. The trifluoroacetic acid was distilled off in vacuo, and the residue stirred with 100 ml ether. 1.7 g beige solid of the title compound were obtained. M.P.=116° C. (dec)

EXAMPLE 10c

2S-[2α,3β(Z)]]-2-[[[1-(2-Amino-4-thiazolyl)-2-[(2-methyl-4-oxo
-1-sulfo-3-azetidinyl)amino]-2-oxoethylidene]-amino]oxy]-2-methylpropanoic acid,
2-[(1,4-dihydro-5-hydroxy-6-methoxy-4-oxo-2-pyridinyl)carbonyl]hydrazide, monopotassium salt.

2.18 g Aztreonam-zwitterion, 1.18 ml n-tributylamine, 0.75 g N-hydroxybenzotriazole monohydrate, 1.1 g DCC and 0.01 g 4-dimethylaminopyridine were dissolved in 40 ml dimethylformamide. After stirring for 1 hour at 10° C., a solution, obtained by stirring 1.67 g of the compound of example 10B with 4 ml MSTFA in 40 ml acetonitrile for 30 minutes, evaporation and redissolving in 10 ml dimethylformamide, was added.

The reaction mixture was stirred overnight, and the formed dicyclohexylurea filtered off. The dimethylformamide of the filtrate was distilled off in vacuo. The residue was dissolved in 50 ml acetone and filtered. To the filtrate were added 3.3 g perfluorobutanesulfonic acid potassium salt dissolved in 50 ml acetone. A biege precipitate of crude title product was obtained. This material was purified by CC on XAD-2, water as eluent. M.P. =255° C. (dec)

EXAMPLE 11

[2S-[2α,3β(Z)]]-2-[[[1-(2-Amino-4-thiazolyl-2-[(2-methyl-4-oxo
-1-sulfo-3-azetidinyl)amino]-oxoethylidene]amino]oxy]-2-methylpropanoic acid,
2-[(1,4-dihydro-3-hydroxy-4-oxo-2-pyridinyl)carbonyl]-hydrazide, monopotassium salt

EXAMPLE 11a 3,4-Bis(phenylmethoxy)-2-pyridinecarboxylic acid,
2-[(1,1-dimethylethoxy)carbonyl]hydrazide 10.05 g 3,4-bis(phenylmethoxy)-2-pyridinecarboxylic acid and 4.44 g N-hydroxybenzotriazole monohydrate were dissolved in 60 ml dimethylformamide. 0.1 g 4-dimethylaminopyridine and 6.18 g dicyclohexylcarbodiimide were added. After stirring for 1 hour at room temperature, 4.35 g t-butoxycarbonylhydrazide were added. After continuous stirring overnight, the formed dicyclohexylurea was filtered off. The filtrate was evaporated in vacuo and the residue dissolved in ethylacetate. The solution was washed with sodium bicarbonate solution, water and dried over sodium sulfate. Distilling off the solvent gave a solid, 12.1 g of the title compound. This was recrystallized from toluene, 10.4 g. FP. 122° C.

EXAMPLE 11b (1,4-Dihydro-3-hydroxy-4-oxo-2-pyridinyl)carbonylcarbamic acid, 1,1-dimethylethyl ester 10 g of the compound from Example 11a were dissolved in 60 ml methanol. 1.0 g Pd/C (10%) was added, and a stream of Hz was bubbled through the reaction mixture for 1 hour. After filtration over "Hyflo", the solvent was distilled off and the residue washed with petrolether yielding 5.90 g of the title compound white solid.

EXAMPLE 11c 1,4-Dihydro-3-hydroxy-4-oxo-2-pyridinecarboxylic acid, hydrazide, trifluoroacetate (1:1) salt 4.0 g of the compound of Example 11B were stirred in 50 ml trifluoroacetic acid and 15 ml anisole. The excess trifluoroacetic acid and the anisole were distilled off in vacuo, and the residue stirred with ether. 4.1 g beige solid of the title compound were obtained.

EXAMPLE 11d

[2S-[2α,3β(Z)]-2-[[[1-(2-Amino-4-thiazolyl-2-[(2-methyl-4-oxo
-1-sulfo-3-azetidinyl)amino]-2-oxoethylidene]aminooxy-2-methylpropanoic acid,
2-[(1,4-dihydro-3-hydroxy-4-oxo-2-pyridinyl)carbonyl]-hydrazide, monopotassium salt

Solution A

To 2.83 g of the compound of Example 11c suspended in 20 ml acetonitrile were added 9.3 ml MSTFA. A clear solution was formed which was stirred for ½ hour. The solvent and formed trimethylsilyltrifluoroacetate were distilled off then in vacuo and the residue dissolved in 20 ml dimethylformamide.

Suspension B 4.36 g Aztreonam zwitterion were dissolved in 40 ml dimethylformamide and 2.40 ml tri-n-butylamine, 1.50 g N-hydroxybenzotriazole and 0.01 g 4-dimethylaminopyridine were added, followed by 2.06 g dicyclohexylcarbodiimide. The mixture was stirred for 30 minutes at room temperature.

Suspension B

A and B were stirred together then at room temperature for 25 hours. The dicyclohexylurea was filtered off and washed with 15 ml tetrahydrofurane. The filtrates were evaporated in vacuo, and the residue dissolved in 80 ml acetone and filtered again. To the fitrate were added 6.7 g perfluorobutanesulfonic acid potassium salt 4.6 g (crude) of the title compound crystallized from the solution. This material was purified on XAD-2, water as eluent. M.P.=270° C. (dec).

EXAMPLE 12

2R-[2α,3β(Z)]]-2-[[[1-(2-Amino-4-thiazolyl)-2-[(2-methyl-4-oxo
-1-sulfo-3-azetidinyl)amino]-2-oxoethylidene]aminooxy]-2-methylpropanoic acid,
2-[[1,4-dihydro-4-hydroxy-6-(pyridinomethyl)-2-pyridinyl]carbonylhydrazide, inner salt.

EXAMPLE 12a 6-(Chloromethyl-4,5-bis(phenylmethoxy)-2-pyridinecarboxylic acid,
2-[(1,1-dimethylethoxy)-carbonyl]hydrazide 8.5 g 6-(Chloromethyl)-4,5-bis(phenylmethoxy)-2-pyridinecarbonyl chloride, monohydrochloride dissolved in 100 ml acetonitrile were added dropwise to a solution obtained from stirring 2.6 g t-butyoxycarbonylhydrazide and 8 g MSTFA in 100 ml acetonitrile for 1 hour. After stirring for 5 hours at 0° C. the solvent was stripped off. The residue was dissolved in 100 ml ethylacetate and washed with water, sodium bicarbonate solution and water. After drying over sodium sulfate the organic phase was evaporated yielding 9.63 g pure of the title compound, white crystals. M.P. 170°-171° C.

EXAMPLE 12b

1-[[6-[[2-[(1,1-Dimethylethoxy)carbonyl]hydrazino]carbonyl]-3,4-bis(phenylmethoxy)-2-pyridinyl]methyl(
pyridinium chloride 9.5 g 6-(chloromethyl)-4,5-bis(phenylmethoxy)-2-pyridinecarboxylic acid, 2-(1,1-dimethylethoxy)carbonyl]hydrazide, 15 ml pyridine, 0.1 g KI and 0.1 g C-18-crown-6 were dissolved in 100 ml dimethylformamide and stirred for 48 hours. After adding 150 ml ether a precipitate of crystals of title compound, white and pure, were obtained, 10.1 g. M.P. 181°-182° C. (dec.)

EXAMPLE 12c

1-[[6-(Hydrazinocarbonyl)-1,4-dihydro-3-hydroxy-4-oxo-2-pyridinyl]methyl]pyridinium chloride,
trifluoroacetate (1:1) salt 8 g of the compound of Example 12b were stirred in 50 ml trifluoroacetic acid/thioanisole (3:2) for 24 hours. After adding 150 ml ether a precipitate of the title compound was obtained, 4.12 g. M.P. 216°-218° C. (dec)

EXAMPLE 12d

[2R-[2α,3β(Z)]]-2-[[[1-(2-Amino-4-thiazolyl)-2-[(2-methyl-4-oxo
-1-sulfo-3-azetidinyl)amino]-2-oxoethylidene]aminooxy]-2-methylpropanoic acid,
2-[[1,4-dihydro-4-hydroxy-6-(pyridinomethyl)-2-pyridinyl]carbonyl]hydrazide, inner salt.

2.18 g of 4-β-methyl Aztreonam-zwitterion, 1.77 g trioctylamine, 0.75 g hydroxybenzotriazole, 1.06 g dicyclohexylcarbodiimide and 0.01 g 4-pyrrolidinopyridine were stirred in 50 ml dimethylformamide for 1 hour at room temperature. This was suspension A. 2.06 g of the compound of Example 12c and 10 g MSTFA were stirred for 1 hour at room temperature in 50 ml CH₃CN. The solvent and formed

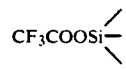

were distilled off then in vacuo. The residue was dissolved in 50 ml dimethylformamide. This was solution B. Solution B and suspension A were stirred together for 20 hours at room temperature. The dicyclohexylurea was filtered of then (1.1 g), and to the filtrate were added 100 ml tetrahydrofuran. A precipitate of 2.4 g crude of the title compound HI 73.6% was obtained. Purification of the title compound yielded a compound having a melting point of 248° C. (dec)

EXAMPLE 13

[2R-[2α,3β(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid.
2-[[6-(aminomethyl)-1,4-dihydro-5-hydroxy-4-oxo-2-pyridinyl]carbonyl]-hydrazide, trifluoroacetate (1:1) salt.

EXAMPLE 13a

6-[[[(1,1-Dimethylethoxy)carbonyl]amino]methyl]4,5-bis(phenylmethoxy)-2-pyridinecarboxylic acid.
2-[(phenylmethoxy)carbonyl]hydrazide 9.41 g 6-[[[(1,1-dimethylethoxy)carbonyl]amino]methyl]-4,5-bis(phenylmethoxy)-2-pyridinecarboxylic acid, 3.09 g HOBT, 0.2 g 4-dimethylaminopyridine and 4.60 g dicyclohexylcarbodiimide were stirred in 50 ml dimethylformamide at room temperature for 30 minutes. Then 3.37 g (phenylmethoxy)carbonylhydrazide in 10 ml (dimethylformamide were dropped in. After stirring overnight the formed dicyclohexylcarbodiimide was filtered off in vacuo. The oily residue was dissolved in ethylacetate and washed with 5% NaHCO₃ solution and then with brine. The organic phase was dried over Na₂SO₄ and evaporated. The residue was stirred with petrolether yielding 12.3 g crude of the title compound as a beige powder. Recrystallization from acetonitrile/water 11.2 g of the title compound. M.P. 128°–129° C.

EXAMPLE 13b

6-[[[(1,1-Dimethylethoxy)carbonyl]amino]methyl]-1,4-dihydro-5-hydroxy-4-oxo-2-pyridinecarboxylic acid.
[2R-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methyl-1-oxopropylhydrazide, monopotassium salt 2.99 g of 4-3-methylaztreonam zwitterion, 2.44 g trioctylamine 1.41 g dicyclohexylcarbodiimide and 1.03 g hydroxybenzotriazole were stirred at 5° C. for 1 hour dimethylformamide = suspension A. A solution of 4.2 g compound from Example 13a and 6 ml MSTFA in 50 ml dimethylformamide was hydrogenated for 1 hour in the presence of 1 g Pd/C (10%). The catalyst was filtered off and washed with dimethylformamide. The filtrate was solution B. A and B were stirred together then for 24 hours at room temperature. The dicyclohexylurea was filtered off, washed with dimethylformamide and the dimethylformamide of the filtrate distilled off. The residue was dissolved in acetone and 3 g perfluorobutanesulfonic acid potassium salt were added. After stirring for 10 minutes ether was added yielding a precipitate of crude title compound. This was purified by CC on Organogen reverse phase resin, water/CH₃CN (9:1) as eluents. Fr. 124–140 contained 1.21 g title compound. M.P. 193°–194° C. (dec).

EXAMPLE 13c

6-[[[(1,1-Dimethylethoxy)carbonyl]amino]methyl]1,4-dihydro-5-hydroxy-4-oxo-2-pyridinecarboxylic acid,
[1R-[2α,3β(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]hydrazide 1.2 g of the compound of Example 13B were suspended in 10 ml H₂O/ice, and the pH was adjusted to 0.2 with 2n HCl. A solution was obtained from which the title compound crystallized out. 0.95 g beige solid. M.P. 134° C. (dec)

EXAMPLE 13d

[2R-2α,3β(Z)]]-2-[[1-(2-Amino-4-thiazolyl)2-[(2-methyl-4-oxo-1-sulfo-3-azetidinyl)amino]-2-oxoethylidene]amino]oxy]-2-methylpropanoic acid.
2-[[6-(aminomethyl)-1,4-dihydro-5-hydroxy-4-oxo-2-pyridinyl]carbonyl]hydrazide, trifluoroacetate (1:1) salt.

0.7 g of the compound of Example 13c were stirred for 45 minutes in 15 ml trifluoroacetic acid at 0° C. 50 ml ether were added then yielding the precipitate of the title compound 0.7 g beige powder. M.P. 218° (dec)

EXAMPLE 14

[2R-[2α,3β(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid.
2-[[1,4-dihydro-5-hydroxy-6-[(1-methyl-1-pyrrolidinyl)-methyl]-4-oxo-2-pyridinyl]carbonyl]hydrazide, inner salt

EXAMPLE 14a

1-[[6-[[2-[(1,1-Dimethylethoxy)carbonyl]hydrazino]carbonyl]-3,4-bis(phenylmethoxy)-2-pyridinyl(methyl]-1-methylpyrrolidinium chloride 2.49 g of the compound of Example 12a 0.1 g KI, 0.1 g C-18-crown-6 and 0.43 g N-methylpyrolidine were stirred in 30 ml dimethylformamide for 4 days and then heated for 1 hour to 70° C. 50 ml ether were added and a precipitate of the title compound was obtained, white crystals, 2.80 g. M.P. 206° C. (dec)

EXAMPLE 14b

1-[[6-Hydrainocarbonyl)-1,4-dihydro-3-hydroxy-4-oxo-2-pyridinyl]methyl]-1-methylpyrrolidium chloride, trifluoroacetate (1:1) salt 2.70 of the compound of Example 14a were stirred in 30 ml trifluoroacetic acid/thioanisole (3:1) for 24 hours. 100 ml ether were added. A precipitate of beige powder of title compound was obtained. M.P. 274° C. (dec)

EXAMPLE 14c

[2R-[2α,3β(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid, 2-[[1,4-dihydro
-5-hydroxy-6[(1-methyl-1-pyrrolidinyl)methyl]-4-oxo-2-pyridinyl]-carbonyl]hydrazide, inner salt 1.33 g of 4-β-methyl aztreonam zwitterion, 0.46 g hydroxybenzotriazole, 1.10 trioctylamine, 0.01 g 4-PP and 0.65 g dicyclohexylcarbodiimide were stirred together in 20 ml dimethylformamide at 5°–10° C. for 1 hour. = Suspension A.

2.1 g chloride, trifluoroacetic acid salt of Example 14b and 3.7 g MSTFA were stirred at room temperature in 30 ml acetonitrile. A clear solution was formed. The solvent and formed SiCl and

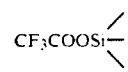

were distilled off in vacuo and the residue was dissolved in 30 ml dimethylformamide = Solution B.

A and B were stirred together for 18 hours at 10° C. The dicyclohexylurea was filtered off then and the dimethylformamide of the filtrate distilled off in vacuo. The residue was stirred with ice water and a few drops of acetic acid at pH 3.5. The precipitate of crude title compound was filtered off then and dried. 1.25 g. The crude compound was purified by column chromatography yielding a compound having a M.P. of 243° C.

EXAMPLE 15

(2R-cis)-1,4-Dihydro-3-hydroxy-4-oxo-2,6-pyridinedicarboxylic acid.
2-[2-[[[1-(2-amino-4-thiozolyl)-2-[(2-methyl-4-oxo-1-sulfo-3-azetidinyl)amino]-2-oxooethylidene]-amino]oxy]-2-methyl-1-oxopropyl]hydrazide, dipotassium salt

EXAMPLE 15a 3,4-Bis(phenylmethoxy)-2,6-pyridinedicarboxylic acid, 6-(phenylmethyl) ester,
2-[2-[(phenylmethoxy)carbonyl]hydrazide]

2.35 g 3,4-Bis(phenylmethoxy)-2,6-pyridinedicarboxylic acid, 6-(phenylmethyl) ester, 0.75 g hydroxybenzotriazole and 1.06 g dicyclohexylcarbodiimide in 30 ml DMF were stirred at room temperature for 1 hour. 1.91 g (phenylmethoxy)carbonalhydrazide were added then and stirring continued overnight. The formed dicyclohexylurea was filtered off and the dimethylformamide of the filtrate distilled off. The residue was purified by column chromatography on SiO₂, ethylacetate/cyclohexane (6:4) as eluents. 1.39 g of title compound were obtained, white crystals. M.P. = 137° C.

EXAMPLE 15b (2R-cis)-1,4-Dihydro-3-hydroxy-4-oxo-2,6-pyridinedicarboxylic acid,
2-[2-[[[1-(2-amino-4-thiozolyl)-2-[(2-methyl-4-oxo-1-sulfo-3-azetidinyl)amino]-2-oxoethylidene]-amino]oxy]-2 TM methyl-1-oxopropyl]hydrazide, dipotassium salt 1.39 g of the compound of Example 15a 0.4 g Pd/C (10%), and 1.79 g MSTFA in 15 ml dimethylformamide were stirred for 1 hour and a stream of H₂ was bubbled through the reaction mixture. The suspension was then filtered and the residue washed two times with 10 ml dimethylformamide. The combined filtrates are solution A.

0.93 g 4-β-methylaztreonam-zwitterion, 0.76 g trioctylamine, 0.33 g N-hydroxybenzotriazole, 0.44 g dicyclohexylcarbodiimide, and 0.03 g 4-pyrrolidinopyridine were stirred in 10 ml dimethylformamide for one hour to the formed suspension solution A was added and stirring was continued for 68 hours at room temperature. The dicyclohexylurea was then filtered off and the dimethylformamide of the filtrate distilled off in vacuo. The residue was dissolved in acetone and 7.2 ml perfluorobutanesulfonic acid potassium salt solution in acetone (10%) was added. A crude precipitate of title compound 1.25 g was obtained. Purification was accomplished by column chromatography. M.P. = 300° (dec).

EXAMPLE 16

[2R-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid,
2-[[6-(aminocarbonyl)-1,4-dihydro-5-hydroxy-4-oxo-2-pyridinyl]carbonyl]hydrazide, monopotassium salt

EXAMPLE 16a 6-(Aminocarbonyl)-4,5-bisiphenylmethoxy)-2-pyridinecarboxylic acid,
2-[(phenylmethoxy)carbonyl]hydrazide 1.90 g 6-(aminocarbonyl)-4,5-bis(phenylmethoxy)-2-pyridinecarboxylic acid, 0.79 g hydroxybenzotriazole 0.1 g 4-PP and 1.09 g dicyclohexylcarbodiimide were stirred in 30 ml dimethylformamide at room temperature for 1 hour. Then 0.89 g (phenylmethoxy)carbonylhydrazide were added. After stirring overnight the formed dicyclohexylurea was filtered off and the dimethylformamide of the filtrate was distilled off. The residue, 1.9 g, was recrystallized from dioxane yielding 1.3 g of the title compound white crystals. M.P. = 176° C.

EXAMPLE 16b 6-(Aminocarbonyl)-1,4-dihydro-5-hydroxy-4-oxo-2-pyridinecarboxylic acid, hydrazide 1.9 g of the compound of Example 16A and 2.1 ml MSTFA and 1 g palladium/carbon were stirred in 30 ml dimethylformamide while a stream of hydrogen was bubbled through the reaction mixture for 1 hour. The catalyst was filtered off and the dimethylformamide of the filtrate distilled off. The residue was stirred with 50 ml isopropanole. 0.9 g white precipitate of title compound were obtained. Recrystallization from dioxane/H₂O. 0.7 g of title compound. M.P. = 255° C.

EXAMPLE 16c

[2R-[2α,3β(Z)]]-2-[[[1-(2-Amino-4-thiazolyl)-2-[(2-methyl-4-oxo
-1-sulfo-3-azetidinyl)amino]-2-oxoethylidene]amino]-oxy]-2-methylpropanoic acid,
2-[[6-(aminocarbonyl)-1,4-dihydro-5-hydroxy-4-oxo-2-pyridinyl]carbonyl]hydrazide, monopotassium salt 1.3 g 4-β-methyl-Aztreonam-zwitterion 0.98 g trioctylamine, 0.5 g N-hydroxybenzotriazole, 0.7 g dicyclohexylcarbodiimide and 0.01 g 4-pyrrolidinopyridine were dissolved in 30 ml dimethylformamide and stirred for 30 minutes at 10° C. = Suspension A.

0.7 g hydrazide of the compound of Example 16b and 2 ml MSTFA were stirred together for 1 hour in 25 ml acetonitrile giving a clear solution B.

A and B were stirred together then for 18 hours first at 0° C. (2 hours) and later at room temperature. The formed dicyclohexylurea was filtered off and the solvents of the filtrate were distilled off in vacuo. The residue (oil) was dissolved in 50 ml acetone, filtered and to the filtrate were added 1.3 g perfluorobutanesulfonic acid potassium salt in acetone. A precipitate of 1.8 g crude title compound was obtained. Purification was accomplished by column chromatography. M.P. = 260° (dec.)

EXAMPLE 17

[2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[(1,4-dihydro-6-cyano-5-hydroxy-4-oxo-2-pyridinyl]-carbonyl]hydrazide, monopotassium salt.

EXAMPLE 17a

6-Cyano-4,5-bis(phenylmethoxy)-2-pyridinecarboxylic acid, 2-[1,1-dimethylethoxy)carbonyl]-hydrazide.

3.51 6-cyano-4,5-bis(phenylmethoxy)-2-pyridine-carboxylic acid, 1.5 g hydroxybenzotriazole, 0.1 g 4-pyrrolidinopyridine and 2.06 g dicyclohexylcarbodiimide were stirred in 50 ml dimethylformamide for 1 hour. 1.2 g BOC-hydrazide were added then and stirring continued overnight. The dicyclohexylurea was filtered off, the dimethylformamide of the filtrate distilled off, and the residue was dissolved in ethylacetate, washed with water, citric acid and sodiumbicarbonate solution and water again. After drying of the organic phase and evaporation, 4.70 g of title compound light yellow solid. M.P.=162° C. (dec)

EXAMPLE 17b

6-Cyano-1,4-dihydro-5-hydroxy-4-oxo-2-pyridinecarboxylic acid, hydrazide, monohydrochloride 3.6 g. of the compound of Example 17a were dissolved in 50 ml trifluoroacetic acid/thioanisole (3:1) and stirred for 24 hours at room temperature. The solvents were distilled off then in vacuo. The oily residue was dissolved in 50 ml 2n Hcl under ice cooling and two times extracted with ether. The water phase was freeze dried and the residue stirred with isopropanol ether. Yield: 0.80 g of title compound, light yellow solid.

EXAMPLE 17c

[2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[(1,4-dihydro-6-cyano-5-hydroxy-4-oxo-2-pyridinyl]-carbonyl]hydrazide, monopotassium salt.

1.17 g 4-β-methyl Aztreonam-zwitterion, 0.95 g tri-octylamine, 0.40 hydroxybenzotriazole 0.55 g dicyclohexylcarbodiimide and 0.001 g 4-pyrrolidino pyridine were stirred in 50 ml dimethylformamide for 1 hour. Yield: suspension A.

0.62 g of the compound of Example 17B and 2.20 g MSTFA were stirred for 30 minutes in 30 ml CH₃CN giving a clear solution. The solvent and formed trimethylchlorosilane were stripped off in vacuo. The remaining oil was dissolved in 20 ml dimethylformamide. This was solution B.

Solution B and suspension A were stirred together for 16 hours at room temperature. The dicyclohexylurea was filtered off then and the dimethylformamide of the filtrate was distilled off in vacuo. The residue was dissolved in 50 ml acetone and a solution of 0.91 g perfluorobutanesulfonic acid, potassium salt was added. The formed precipitate was crude title compound, 1.8 g (HI 53.7%). Purification was accomplished by column chromatography. M.P.=>300° C.

EXAMPLE 18

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[6-[[(aminocarbonyl)amino]methyl]-1,4-dihydro-5-hydroxy-4-oxo-2-pyridinyl]carbonyl ]-hydrazide, monopotassium salt

EXAMPLE 18a 6-(Aminomethyl)-4,5-bisiphenylmethoxy)-2-pyridinecarboxylic acid, 2-[(phenylmethoxy)carbonyl]-hydrazide, trifluoroacetate (1:1) salt 4.20 g of the compound of Example 13a, in 30 ml CH₂Cl₂ and 30 ml trifluoroacetic acid were stirred at 0° C. for 1 hour. 100 ml ether were added -yielding a precipitate of the title compound, white crystals, 4.30 g. M.P.=176°-178° C.

EXAMPLE 18b

6-[[(Aminocarbonyl)amino]methyl]-4,5-bis(phenylmethoxy)-2-pyridinecarboxylic acid,
2-[(phenylmethoxy)carbonyl]hydrazide 3.70 g (5.9 mmol) of the compound of Example 18a were suspended in 100 ml CH₃CN and 3.3 ml MSTFA were added upon which a homogenous solution was obtained. After the mixture had been stirred at room temperature for 1 hour, the solvent was evaporated, finally at 0.5 mm. The residue was dissolved in 100 ml tetrahydrofuran and 0.65 g (6.2 mmol) ClCONCO was added dropwise at 5° C. After 2.5 hours, 2.0 ml water was added and the reaction mixture was stirred for 20 minutes. The solvent was evaporated and the residue was worked upon with EtOAc and water/bicarbonate. The organic phase was dried (MgSO₄), evaporated and the residue stirred with hexane to give 3.2 g of a solid which was dissolved in tetrahydrofuran and chromatographed on silica with cyclohexane/tetrahydrofuran (7:3). 1.1 g of pure title compound (33.5%) were obtained, m.p. 199°-201° C.

EXAMPLE 18c

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[6-[[(aminocarbonyl)amino]methyl]-1,4-dihydro-5-hydroxy-4-oxo-2-pyridinyl]carbonyl ]-hydrazide, monopotassium salt

Solution A 1.1 ml MSTFA were added to a solution of 1.1 g of the compound of Example 18b in 25 ml dimethylformamide and 0.5 g palladium/carbon (10%). Hydrogen was bubbled through under vigorous stirring for 1 hour. The catalyst was filtered off then. The filtrate was Solution A.

Suspension B 0.78 g 4-β-methylaztreonam-zwitterion were dissolved in 15 ml dimethylformamide, and 0.78 ml trioctylamine were added. After stirring for 15 minutes, 0.27 g hydroxybenzotriazole (containing 13% H₂O), 0.37 g dicyclohexylcarbodiimide and 3 mg of 4-PP were added. The mixture was stirred for 30 minutes after which time dicyclohexylurea had precipitated.

Solution A was added to Suspension B, and the mixture was stirred at room temperature for 15 hours. The precipitate was filtered off, and the filtrate was evaporated in vacuo. The residue was triturated with 20 ml acetone and filtered. The clear filtrate was treated with 0.7 g perfluoropotassiumbutanesulfonate (dissolved in a little acetone), and the resulting precipitate was collected by filtration to give 0.7 g of title compound. HI=82%. Another 0.6 g of title compound, HI=92%, were precipitated from the mother liquors by the addition of ether. Total crude yield: 1.3 g (94.2%) Purification: 1.0 g of the crude material was purified by column chromatography on Organogen, first with water (1000 ml), then with water/CH$_3$CN (9:1). M.P.=249° C. dec.

EXAMPLE 19

2R-[2α,3β(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[6-[[(aminocarbonyl)amino]methyl]-1,4-dihydro-5-hydroxy-4-oxo-2-pyridinyl]carbonyl
]-hydrazide-4-potassium salt

EXAMPLE 19A 6-(Hydrazinocarbonyl)-4,5-bisiphenylmethoxy)-2-pyridinecarboxylic acid 4g 3,4-Bis(phenylmethoxy)-2,6-pyridinedicarboxylic acid, 6-(phenylmethyl) ester were dissolved in 150 ml tetrahydrofuran. The solution was dropped into a solution of 2.5 equivalents of hydrazine (free of water) in tetrahydrofuran and stirred for 12 hours. A white precipitate of the hydrazine salt of the title compound was obtained. This was stirred with 2n HCl at pH 1 in water, filtered off and washed with water. 3.2 g white solid after drying. M.P. =262° C. (dec)

EXAMPLE 19b 6-(Hydrazinocarbonyl)1,4-dihydro-5-hydroxy-4-oxo-2-pyridinecarboxylic acid 3 g of the title compound of Example 19A and 6.6 ml MSTFA in 50 ml dimethylformamide were stirred until a clear solution was formed. 1 g palladium/carbon (10%) catalyst was added and a stream of hydrogen was bubbled through the reaction mixture for 1 hour. The catalyst was filtered off then and washed with dimethylformamide. The dimethylformamide of the filtrate was distilled off and the residue stirred with 100 ml isopropanol. Yield: white precipitate of title compound 1.5 g. M.P.=198° C. (dec.)

EXAMPLE 19c

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[6-[[(aminocarbonyl)amino]methyl]-1,4-dihydro-5-hydroxy-4-oxo-2-pyridinyl]carbonyl
]-hydrazide-dipotassium salt 1 g 4β-methylaztreonam-zwitterion, 0.9 g trioctylamine, zwitterion 0.5 g hydroxybenzotriazole (dried) and 0.6 g dicyclohexylcarbodiimide were stirred at 15°-20° C. for 2 hours in 30 ml dimethylformamide. The formed dicyclohexylurea was filtered off and washed with dimethylformamide. The filtrate was solution A.

0.5 g of the compound of Example 19b and 2.2 ml MSTFA were stirred in 20 ml acetonitrile for 1 hour giving a clear solution=solution B.

Solution A was added dropwise to solution B at 0° C after continuous stirring for 24 hours. The dimethylformamide was distilled off and the residue dissolved in acetone/methanol. After adding 2 g perfluorobutanesulfonic acid potassium salt in acetone a precipitate of crude 19c was obtained. 1.3 g. This was purified by column chromatography on Organogen (reverse phase silica gel) water as eluent. M.P.=299° C. (dec).

EXAMPLE 20

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[1,4-dihydro-5-hydroxy-6-[[(1-methyl-4-pyridinio]-thio]methyl]-2-pyridinyl]carbonyl]-hydrazide, inner salt

EXAMPLE 20a 4,5-Bis(phenylmethoxy)-6-[(4-pyridinylthio)methyl]-2-pyridinecarboxylic acid,
2-[(1,1-dimethylethoxy)carbonyl]hydrazide 4.98 g of the compound of Example 12A, 1.01 g triethylamine and 1.12 g 4-mercaptopyridine in 30 ml dimethylformamide were stirred at 60° C. for 4 hours. The dimethylformamide was distilled off then, and the residue stirred with water/ethylacetate. The organic phase was dried and evaporated yielding 5.70 g of the compound light yellow crystals, recrystallized from water/ dioxane. M.P.=181°-182° C.

EXAMPLE 20b

4-[[[6-[[2-[(1,1-Dimethylethoxy)carbonyl]-hydrazino]-carbonyl]-3,4-bis(phenylmethoxy)-2-pyridinyl]methyl]-thio]-1-methylpyridinium iodide 2.7 g of the compound of Example 20a and 1.3 g methyliodide were stirred in 30 ml dimethylformamide for 48 hours. Complete reaction by DC after that time. The dimethylformamide was distilled off and the residue stirred with ether yielding 3.3 g of the title compound, yellow solid. M.P.=192°-193° C. (dec).

EXAMPLE 20c

4-[[[6-(Hydrazinocarbonyl)-1,4-dihydro-5-hydroxy-4-oxo-2-pyridinyl]methyl]thio]-1-methyl-pyridinium iodide, trifluoroacetate (1:1) salt 3.2 g of the compound of Example 20b were stirred in 30 ml trifluoroacetic acid/thioanisole for 24 hours at room temperature. 100 ml ether were added. A precipitate of the title compound was obtained, yellow solid, 2.32 g. M.P. 232°-33° C. dec.)

EXAMPLE 20d

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[1,4-dihydro-5-hydroxy-6-[[(1-methyl-4-pyridinio)-thio]methyl]-2-pyridinyl]carbonyl]-hydrazide, inner salt 1 g of 4β-methyl aztreonam-zwitterion, 0.8 g trioctylamine, 0.4 g hydroxybenzotriazole (dried) and 0.56 g dicyclohexylcarbodiimide were stirred in 30 ml dimethylformamide at 5° C. for two hours. The filtrate of the reaction was solution A. 1.1 g of the compound of Example 20c and 3.1 MSTFA were stirred in 15 ml acetonitrile for 1 hour. After evaporation the residue dissolved in 15 ml dimethylformamide was solution B.

To solution B was dropwise added solution A and after continuous stirring for 24 hours at 5° C the solvent was distilled off and the residue stirred with water at pH 5.5 The precipitate of crude title compound. 1.3 g (HI 25%) purified on XAD-2 (water/CH$_3$CN gradient). M.P.=300° C.(dec.)

EXAMPLE 21

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid.
2-[[1,4-1,4-dihydro-5-hydroxy-6-(hydroxymethyl)-2-pyridinyl]carbonyl]hydrazide, monopotassium salt 1.09 g 4-β-methyl Aztreonam-zwitterion, 0.89 g trioctylamine, 0.37 g N-hydroxybenzotriazole, 0.53 g dicyclohexylcarbodiimide and 0.001 g 4-pyrrolidinopyridine were stirred for 1 hour in 50 ml dimethylformamide. The formed dicyclohexylurea was filtered off then and washed with 10 ml dimethylformamide. The filtrate was solution A 0.78 g of the compound of Example 9C and 2.50 g MSTFA were stirred in 50 ml acetonitrile for 1 hour. The solvent and formed trifluoroacetic acid trimethylsilylester were distilled off in vacuo, and the residue dissolved in 20 ml dimethylformamide. This was solution B.

Solutions A and B were combined and stirred for 12 hours at room temperature. The solvent was distilled off then in vacuo, and the residue dissolved in 50 ml acetone. A solution of 0.9 g perfluorobutane sulfonic acid potassium salt in 20 ml acetone was added. A precipitate of crude title compound was obtained. It was isolated by filtration, washed with acetone and ether. 1.4 g beige HI 76.9% was obtained by adding 50 ml diethylether. The 1.4 g were purified by column chromatography on reverse phase Organogen, water as eluent. M.P.=>300° C.

EXAMPLE 22

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]cyclopentanecarboxylic acid,
2-[[1,4-dihydro-5-hydroxy-6-(hydroxymethyl)-4-oxo-2-pyridinyl]carbonyl]-hydrazide, monopotassium salt 1.91 g [2S-[2α,3α(Z)]]-1-1-(2-Amino-4-thiazolyl)-2-(2-methyl-4-oxo-1-sulfo-3-azetidinyl)amino]-2-oxoethylidene]amino]oxy]cyclopentanecarboxylic acid, zwitterion 1.46 g trioctylamine, 0.63g hydroxybenzotriazole, 0.85 dicyclohexylcarbodiimide and 0.06 g 4-pyrrolidinopyridine were dissolved in 20 ml dimethylformamide and stirred for 1 hour at room temperature. This suspension was A. 1.29 g trifluoroacetic acid salt of the compound of Example 9c and 4.11 g MSTFA were stirred for one hour in 20 ml acetonitrile, and the solvent and the formed trimethylsilyltrifluoroacetate were distilled off then. The residue dissolved in 10 ml dimethylformamide was solution B.

A and B were stirred overnight at room temperature. The dicyclohexylurea was filtered off then and the dimethylformamide of the filtrate was distilled off in vacuo. The residue was dissolved in 20 ml acetone and filtered. To the filtrate was added a solution of perfluorobutanesulfonic acid potassium salt in acetone (140 ml; 10%). A precipitate of 2.1 g crude title compound was obtained.

Purification of title compound on reverse phase Organogen; water and water/acetonitrile (9:1) as eluents. M.P.=>300° C.

EXAMPLE 23

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]cyclopentanecarboxylic acid,
2-[[6-(aminomethyl)-1,4-dihydro-5-hydroxy-4-oxo-2-pyridinyl)carbonyl]hydrazide, monopotassium salt/ trifluoroacetate (1:1) salt

EXAMPLE 23a

6-[[[(1,1-Dimethylethoxy)carbonyl]amino]methyl]-1,4-dihydro-5-hydroxy-4-oxo-2-pyridinecarboxylic acid
[2R-[2α,3α(Z)]]-2-[[1-[[[1-(2-amino-4-thiazolyl)-2-[(2-methyl-4-oxo-1-sulfo-3-azetidinyl)amino]-2-oxoethylidene]amino]-2-oxoethylidene]amino]oxy]cyclopentyl]carbonyl]hydrazide monopotassium salt 1.38 g
[2R-[2α,3α(Z)]]-1-[[[1-(2-Amino-4-thiazolyl)-2-[(2-methyl-4-oxo-1-sulfo-3-azetidinyl)amino]-2-oxoethylidene]amino]oxy]cyclopentanecarboxylic acid, zwitterion, 1.0 g trioctylamine. 0.5 g hydroxyenzotriazole, 0.01 g 4-pyrrolidinopyridine and 0.7 g dicyclohexylcarbodiimide in 30 ml dimethylformamide were stirred for 1 hour at 10° C =Suspension A. 0.8 g
6-[[(1,1-Dimethylethoxy)carbonyl]-amino]methyl]-1,4-dihydro-5-hydroxy-4-oxo-2-pyridinecarboxylic acid, hydrazide and 2 ml MSTFA in 30 ml acetonitrile were stirred for 1 hour. Solution B.

A and B were stirred together then for 24 hours. The dicyclohexylurea was filtered off and the solvents of the filtrate were distilled off in vacuo. The residue dissolved in 50 ml acetone was filtered and to the filtrate was added a solution of 1.5 g perfluorobutanesulfonic acid potassium salt, followed by 50 ml ether. After stirring for 10 minutes 2.2 g crude was filtered off. Purification of crude title compound by column chromatography on Organogen, water/acetonitrile gradient (0.5→10%) acetonitrile as eluent.

EXAMPLE 23b

2R-[2α,3α(Z)]]-1-[[[1-(2-Amino-4-thiazolyl)-2-[(2-methyl-4-oxo-1-sulfo-3-azetidinyl)amino]-2-oxoethylidene]amino]oxy]cyclopentanecarboxylic acid,
2-[[6-(aminomethyl)-1,4-dihydro-5-hydroxy-4-oxo-2-pyridinyl)carbonyl]hydrazide, monopotassium salt trifluoroacetate (1:1)-salt 0.24 g of the compound of Example 23A (HI 92.9%) were stirred at −10° C. with 20 ml trifluoroacetic acid for 45 minutes. After adding 100 ml ether, a precipitate of 0.18 g of the title compound was obtained. M.P.=250° C. (dec.)

EXAMPLE 24

[2S-[2α,3β(Z)]]-1-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
2-[[6-(aminomethyl)-1,4-dihydro-5-hydroxy-4-oxo-2-pyridinyl]carbonyl]-hydrazide, monopotassium salt,
trifluoroacetate (1:1) salt

EXAMPLE 24a

6-[[[(1,1-Dimethylethoxy)carbonyl]amino]methyl]-1,4-dihydro-5-hydroxy-4-oxo-2-pyridinecarboxylic acid,
2S-2α,3β(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]hydrazide,
monopotassium salt 1.1 g of aztreonam-zwitterion, 0.88 trioctylamine, 0.4 g hydroxybenzotriazole, 0.01 g 4-pyrrolidinopyridine and 0.6 g dicyclohexylcarbodiimide in 30 ml dimethylformamide were stirred for hour at 10° C. The formed suspension was A. 0.7 g of 6-[[[(1,1-dimethylethoxy)carbonyl]amino]-methyl]-1,4-dihydro-5-hydroxy-4-oxo-2-pyridinecarboxylic acid, hydrazide and 2 ml MSTFA were stirred for 1 hour in 30 ml acetonitrile -yielding a clear solution B.

A and B were stirred together for 24 hours then at room temperature. The formed dicyclohexylurea was filtered off and the solvents of the filtrate were distilled off in vacuo. The oily residue was dissolved in 50 ml acetone, filtered and to the filtrate was added a solution of 1 g perfluorobutanesulfonic acid potassium salt in 15 ml acetone. 50 ml ether were added and the precipitate of crude title compound, 2.1 g. was isolated, HI 83.3%. This material was purified by column chromatography on a reverse phase Organogen column with a water-/acetonitrile gradient (0.5→5% acetonitrile).

EXAMPLE 24b

[2S-[2α,3β(Z)]]-1-[[1-(2-Amino-4-thiazolyl)-2-[(2-methyl-4-oxo
-1-sulfo-3-azetidinyl)amino]-2-oxoethylidene]amino]oxy-2-methylpropanoic acid,
2-[[6-(aminomethyl)-1,4-dihydro-5-hydroxy-4-oxo-2-pyridinyl]carbonyl]-hydrazide, monopotassium salt,
trifluoroacetate (1:1) salt 0.37 g of the compound of Example 24A (HI 99.1) in 20 ml trifluoroacetic acid were stirred for 45 minutes at − 10° C. After adding 100 ml ether a precipitate of title compound was obtained, 0.3 g. M.P.=235° C.

EXAMPLE 25

[2R-[2α,3α(Z)]]-[[[1-(2-Amino-4-thiazolyl)-2-[(2-methyl-4-oxo-1-sulfo-3-azetidinyl)amino]-2-oxoethylidene]amino]oxy]acetic acid,
2-[(6-aminoethyl)-1,4-dihydro-5-hydroxy-4-oxo-2-pyridinyl)carbonyl]hydrazide, monopotassium salt,
trifluoroacetate (1:1) salt

EXAMPLE 25a

6-[[[(1,1-Dimethylethoxy)carbonyl]amino]-methyl]-1,4-dihydro-5-hydroxy-4-oxo-2-pyridinecarboxylic acid,
12R-2α,3α(Z)]]-2-[[[[1-(2 TM amino-4-thiozolyl)-2-[(2-methyl-4
-oxo-1-sulfo-3-azetidinyl)-amino]-2-oxoethylidene]amino]oxy]acetyl]-hydrazide,
monopotassium salt 1.02 g of 4-β-methylaztreonam-zwitterion, 0.34 g hydroxybenzotriazole, 0.47 g dicyclohexylcarbodiimide and 0.1 g 4-pyrrolidinopyridine were stirred in 30 ml dimethylformamide for 1 hour. A solution of 0.75 g of the compound of Example 9b and 2.51 g MSTFA in 30 ml CH₃CN was then added. After continuous stirring overnight the formed dicyclohexylurea was filtered off and the filtrate solvents distilled off in vacuo. The residue was dissolved in acetone and 1.5 g perfluorobutanesulfonic acid potassium salt were added. After stirring for 30 minutes 50 ml ether were added yielding a precipitate of crude title compound, 1.93 g. This was purified by column chromatography on Organogen water/CH₂CH as eluents (3→10% CH₃CN). 0.76 g purified title compound were obtained.

EXAMPLE 25b

2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]acetic acid,
2-[(6-aminoethyl)-1,4-dihydro-5-hydroxy-4-oxo-2-pyridinyl)carbonyl]hydrazide, monopotassium salt,
trifluoroacetate (1:1) salt 0.35 g of the compound of Example 25a were stirred at − 10° C. for 45 minutes in 20 ml trifluoroacetic acid. 100 ml ether were added and the precipitate isolated by filtration and washed with ether and dried. 0.31 g of title compound. M.P.=230° C. (dec).

EXAMPLE 26

2R-[2α,3α(Z,S)]]-2-[[[1-(2-Amino-4-thiazolyl)-2-[(2-methyl-4-oxo
-1-sulfo-3-azetidinyl)amino]-2-oxo-ethylidene]amino]oxy]propanoic acid,
2-[[6-(aminomethyl)-1,4-dihydro-5-hydroxy-4-oxo-2-pyridinyl]carbonyl]hydrazide, trifluoro acetate (1:3) salt

EXAMPLE 26a

2R-[2α,3α(Z,S]]-2-[[[1-(2-Amino-4-thiazolyl)-2-[(2-methyl-4-oxo
-1-sulfo-3-azetidinyl)amino]-2-oxo-ethylidene]amino]oxy]propanoic acid,
2-[[6-(aminomethyl)-1,4-dihydro-5-hydroxy-4-oxo-2-pyridinyl]hydrazide, monopotassium salt 0.69 g [2R-[(2α;3a(Z,S)]]-2-[[[1-(2-Amino-4-thiazolyl)-2-[(2-methyl -4-oxo-1-sulfo-3-azetidinyl-)amino]-2-oxoethylidene]amino]oxy]propanoic acid, 0.25 g hydroxybenzotriazole, catalytic amounts of 4- pyrrolidinopyridine and 0.37 g dicyclohexylcarbodiimide were dissolved in 20 ml dimethylformamide and stirred at 0° C. for 1 hour = suspension A.

0.49 g 6-[[[(1,1-dimethylethoxy)carbonyl]amino]methyl[-1,4-dihydro-5-hydroxy-4-oxo-2-pyridinecarboxylic acid, hydrazide and 0.58 g trioctylamine were dissolved in 10 ml dimethylformamide = solution B.

B was then added to A at −20° C. and stirred for 24 hours at room temperature. The formed dicyclohexylurea was then filtered off in vacuo and the residue dissolved in acetone. 1.71 g perfluorobutanesulfonic acid potassium salt dissolved in acetone was added. A precipitate of title compound was obtained. 1.08 g. Purification of title compound by column chromatography on HP-20 resin (water/acetonitrile gradient 9:1→7:3).

0.14 g free acid of the compound of Example 26a (obtained form Example 26a at pH 2.5 in water) was stirred with 10 ml trifluoroacetic acid at −10° C. for 1 hour. After adding 50 ml ether a precipitate of 0.12 g title compound. M.P. > 205° C. (dec.), was obtained.

EXAMPLE 27

[2R-[2α,3α(Z,S)]]-2-[[1-(2-Amino-4-thiazolyl)-2-[(2-methyl-4-oxo
-1-sulfo-3-azetidinyl)amino]-2-oxoethylidene]amino]oxy]propanoic acid,
2-[[6-aminomethyl)-1,4-dihydro-5-hydroxy-4-oxo-2-pyridinyl]carbonyl]hydrazide 3.1 g of the compound of Example 26 were dissolved in 15 ml ice water, the pH was adjusted with NaOH to 5.8. A precipitate of title compound was obtained and filtered off after stirring for 15 minutes at 5° C. 2.25 g title compound was obtained after washing with 25 ml ice water. M.P. = > 210° C. (dec).

EXAMPLE 28

6-Aminomethyl)-1,4-dihydro-4-oxo-2-pyridine carboxylic acid, monohydrochloride

EXAMPLE 28a

6-[[[(1-,1-Dimethylethoxy)carbonyl]amino]-methyl]-1,4-dihydro-5-hydroxy-4-oxo-2-pyridinecarboxylic acid 3.94 g 6-[[[(1,1-Dimethylethoxy)carbonyl]amino]methyl]-4,5-bis(phenylmethoxy)-2-pyridinecarboxylic acid and 1.3 g palladium/carbon (10%) were suspended in 70 ml methanol. Hydrogenation at normal pressure completed the reaction after one hour. The catalyst was then filtered off and washed with dimethylformamide. The combined filtrates were evaporated and the residue stirred with ether. 2 g of title compound were obtained as a white powder. M.P. = > 300° C.

EXAMPLE 28b

6-Aminomethyl)-1,4-dihydro-4-oxo-2-pyridine carboxylic acid, monohydrochloride 1.92 g of the compound of Example 28a were stirred with 30 ml tetrahydrofuran and 30 ml HCl (17%) for two hours at 40° C. Crystals of the compound of Example 9a were formed after 2 hours. The suspension was added to 50 ml tetrahydrofuran and after standing in the refrigerator for several hours, 1.43 g of title compound was isolated. M.P. 285° C.

EXAMPLE 29

4-(Aminocarbonyl)-1-[[6-[[2-[(1,1-dimethylethyloxy)-carbonyl]hydrazino]carbonyl]-3,4-bis (phenylmethoxy)-2-pyridinyl]methyl]pyridinium chloride 4.98 g 6-(chloromethyl)-4,5-bis(phenylmethoxy)2-pyridinecarboxylic acid, 2-[(1,1-dimethylethoxy)carbonyl]hydrazide and 1.23 g of isonicotine acid hydrazide and 0.1 g KI and 0.1 g C-18-Crown-6 were stirred for 12 hours at 50° C. in 50 ml dimethylformamide. After filtration the dimethylformamide was distilled off in vacuo and the residue stirred with ether. A yellow solid was obtained. 6.20 g of title compound. M.P. 205°–208° C. (dec.)

EXAMPLE 30

4-(Aminocarbonyl)-1-[[6-(hydrazinocarbonyl)-1,4-dihydro-3-hydroxy-4-oxo-2-pyridinyl]-methyl]pyridinium chloride, trifluoroacetate (1:1) salt 6 g of the compound of Example 29 were dissolved in 50 ml trifluoroacetic acid/thioanisole (3:1) and stirred for 24 hours at room temperature. After adding 200 ml ether a precipitate of the title compound was obtained.

EXAMPLE 31

2R-[2α,3α(Z)]]-4-(Aminocarbonyl)-1-[[6-[[2-[2-[[[1-(2-
-amino-4-thiazolyl)-2-[(2-methyl-4-oxo-1-sulfo-3-
azetidinyl]amino-2-oxoethylidene]amino]oxy]-2-methyl-1-oxopropyl]hydrazino]carbonyl]1,4-dihydro-3-hydroxy-4-oxo-2-pyridinyl]methyl]pyridinium inner salt Solution A 1.4 g 4,β-methylaztreonam zwitterion, 1 g trioctylamine, 0.55 g N-hydroxybenzotriazole and 0.75 g dicyclohexylcarbodiimide were stirred in 30 ml dimethylformamide for 1 hour at room temperature. The formed dicyclohexylurea was filtered off and washed with 10 ml dimethylformamide. Filtrate - solution A.

Solution B 1.1 g of the compound of Example 30 dissolved in 25 ml acetonitrile were stirred with 4 ml MSTFA for 1 hour. The acetonitrile and the volatiles were distilled off in vacuo and the oily residue dissolved in 15 ml dimethylformamide (Solution B)

Solution B was dropped into solution A at 0° and stirred overnight at room temperature. The dimethylformamide was then distilled off in vacuo and the residue stirred with 20 ml tetrahydrofuran until it became solid. 0.75 g brown solid crude title compound 31.

Purification by MPLC on a Organogen reverse phase column water/acetonitrile was used as eluent. M.P. > 240° C.

EXAMPLE 32

6-[[(Carboxymethyl)thio]methyl]-4,5-bis(phenylmethoxy)-2-pyridinecarboxylic acid, methyl ester To 5.96 g of 6-(chloromethyl)-4,5-bis(phenylmethoxy)-2-pyridinecarboxylic acid, methyl ester 0.25 g KI dissolved in 30 ml dimethylformamide, was added a solution of 1.38 g mercaptoacetic acid and 3.04 g triethylamine in 30 ml dimethylformamide. After stirring overnight the formed triethylamne/HCl was filtered off, and the dimethylformamide of the filtrate distilled off in vacuo. The residue was stirred with water/ethylacetate and the pH was adjusted to 2 with 2n HCl. The organic phase was washed with water, dried and evaporated. 6.8 g solid of title compound. Crystallization from ethanol yielded 3.01 g title compound and from the concentrated filtrate another batch of 0.37 g title compound was obtained. M.P. 135° C.

EXAMPLE 33

6-[[(Carboxymethyl)thio)methyl]-4,5-bis(phenyl)methoxy)-2-pyridinecarboxylic acid, hydrazide 3.17 g of the compound of Example 32 dissolved in 50 ml dioxane were added dropwise to a solution of 0.67 g hydrazine in dioxane at 0° C. After a short time a suspension was formed. Stirring was continued for 24 hours. The precipitate was filtered off. It was the hyrazine salt of the title compound. The material was dissolved in 100 ml H₂O and the pH was adjusted to pH 4.5 with acetic acid. A precipitate of 2.6 g title compound white crystals was obtained. M.P. 181° C.

EXAMPLE 34

6-(Azidomethyl)-4,5-bisiphenylmethoxy)-2-pyridinecarboxylic acid, 2-[(1,1-dimethylethoxy)carbonyl]hydrazide 6.2 g of 6-(azidomethyl)-4,5-bis(phenylmethoxy)-2-pyridinecarboxylic acid 2.43 g hydroxybenzotriazole and 3.60 g dicyclohexylcarbodiimide and 0.24 g 4-pyrrolidino pyridine were stirred in 30 ml dimethylformamide for 1 hour at 5° C. After that time a solution of 2.10 g BOC hydrazide in 10 ml dimethylformamide was added dropwise. Stirring was continued for 20 hours. The dicyclohexylurea formed was filtered off and the dimethylformamide of the filtrate distilled off in vacuo. The residue was dissolved in ethylacetate and washed with sodiumbicarbonate solution and water. From the dried and evaporated organic phase 8.3 g yellow crystals of title compound were obtained. Recrystallization from ethanol yielded 6.4 g of title compound. M.P. = 103° C.

EXAMPLE 35

[2R-[2α(Z,S)]]-2-[[[1-(2-Amino-4-thiazolyl)-2-[(2-methyl-4-oxo-1-sulfo-3-azetidinyl)amino]2-oxoethylidine]amino]oxy]propanoic acid, dipotassium salt

EXAMPLE 35a

[2R-[2α,3α(Z,S*)]]-2-[[[1-(2-Amino-4-thiazolyl)-2-[(2-methyl-4oxo-1-sulfo-3-azetidinyl)amino]-2-oxoethylidene]amino]oxy]propanoic acid, diphenylmethyl ester, monopotassium salt 25.53 g S-(Z)]-2-Amino-α-[2-(diphenylmethoxy)-1-methyl-2-oxoethoxy]imino]-4-thiazoleacetic acid; 9.31g hydroxybenzotriazole; 12.38 g dicyclohexylcarbodiimide; and a few crystals of 4-pyrrolidinopyridine were dissolved in 400 ml dimethylformamide and stirred at 0°-5° C. for 90 minutes. After cooling down to −20° C. a solution of 10.81 g (2R-cis)-3-amino-2-methyl-4-oxo-1-azetidine-sulfonic acid, inner salt and 26.33 ml trioctylamine in 200 ml dimethylformamide was added dropwise while stirring. After continuous stirring overnight at room temperature the formed dicyclohexylurea was filtered off and washed with dimethylformamide. The dimethylformamide of the filtrate was distilled off in vacuo and the oily residue dissolved in 150 ml acetone. To the again filtered acetone solution 22.32 g perfluorobutanesulfonic acid potassium salt were added. A precipitate of 37.33 g of title compound was obtained.

EXAMPLE 35b

[2R-[2α(Z,S)]]-2-[[[1-(2-Amino-4-thiazolyl)-2-[(2-methyl-4-oxo-1-sulfo-3-azetidinyl)amino]2-oxoethylidine]amino]oxy]propanoic acid, dipotassium salt To 37.25 g of the compound of Example 35a, suspended in 20 ml methylenechloride/40 ml anisole, 200 ml trifluoroacetic acid were added dropwise at −10° C. During 45 minutes first a solution and the a suspension was obtained. To the mixture was then added 1000 ml ether while cooling. A precipitate of 28.57 g. trifluoroacetic acid salt of title compound was obtained. This material was dissolved in ice water and the pH was adjusted to 5.5 with potassium hydroxide solution. After extraction with 100 ml ether the water-phase was freeze dried. 48.63 g crude title compound. Purification of title compound by MPLC on HP20 resin. Water as an eluent. 20.62 g title compound were obtained. M.P. >200° C. (dec.)

EXAMPLE 36

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid 2-[[6-(aminomethyl)-1,4-dihydro-5-hydroxy-4-oxo-2-pyridinylcarbonyl]-2-methylhydrazide

EXAMPLE 36a

1-Methylhydrazinecarboxylic acid, 1,1-dimethylethyl ester

To a solution of methyl hydrazine (2.3 g, 50 mmol) in 200 ml water/tetrahydrofuran 1:1 di-tert-butyl-dicarbonate (10.91 g, 50 mmol) was added and the pH of the solution was kept at 8-9 with 2N sodium hydroxide solution. The solution was stirred overnight at room temperature with a pH of 8-9. The tetrahydrofuran was distilled off in vacuo and the residue extracted three time with ethylacetate. The organic phase was washed with water and dried over sodium sulfate. After filtration the ethylacetate was distilled off in vacuo on a rotary evaporator and subsequently, at oil pump vacuo, the desired product was distilled. Yield 3.68g.

EXAMPLE 36b

1-Methyl-1,2-hydrazinedicarboxylic acid 1-(1,1-dimethylethyl]-2-(phenylmethyl) ester To a solution of the compound of Example 36a (4.0 g, 27.4 mmol) in 80 ml water/tetrahydrofuran 1:1 with pH 8 a solution of benzylchloroformate (4.67g, 27.4 mmol) was added dropwise. Simultaneously 2N NaOH aqu. solution were added to keep the pH at 8. After stirring for 2 days, tetrahydrofuran was distilled off in vacuo and the residue extracted three times with ethyl acetate. The organic phase was washed with water and dried over sodium sulfate. After filtration the solvent was distilled off in vacuo to give the desired product a colorless oil. Yield 7.21 g.

EXAMPLE 36c

2-Methylhydrazinecarboxylic acid phenylmethyl ester

To a suspension of the compound of Example 36b, (6.93 g, 24.7 mmol) in 6.9 ml anisole 70 ml trifluoroacetic acid were added dropwise at 0° C. After stirring for one hour the volatiles were distilled off in vacuo to give the trifluoroacetic acid salt of the desired product as an oil (8.39 g). 6.6 g of this oil were dissolved in 100 ml water/ethylacetate 1:1 and one equivalent triethylamine was added. After thorough stirring for 10 minutes the organic phase was separated, the aqueous phase extracted with ethylacetate and the combined organic phases washed with water and brine. After drying the solvent was removed in vacuo to give the desired product as pale crystals. Yield 3.39 g. M.P. 71°–73° C.

EXAMPLE 36d

6-[[[(1,1-Dimethylethoxy)carbonyl]amino]methyl]-4,5-bis(phenylmethoxy)-2-pyridinecarboxylic acid, 1-methyl-2-[(phenylmethoxy)carbonyl]hydrazide To a solution of 6-[[(1,1-dimethylethoxy)carbonyl]amino]methyl]-4,5-bis(phenylmethoxy)-2-pyridinecarboxylic acid, (0.46 g. 1.0 mmol) in 10 ml dimethylformamide N-hydroxybenzotriazole (0.135 g. 1.0 mmol), dimethylaminopyridine (6 mg. 50 µl) and dicyclohexyl carbodiimide (0.25 g. 1.2 mmol) were added and the mixture was stirred for 2 hours at room temperature. The compound of Example 36c (0.18 g. 1.0 mmol) was added and after stirring overnight dicyclohexylurea was filtered off and the solvent distilled off in vacuo. The residue was dissolved in 50 ml water/ethylacetate 1:1, the phases were separated and the aqueous phase extracted three times with ethyl acetate. The combined organic phases were dried and after evaporation 0.62 g silica gel with ethyl acetate as eluent to give 0.38 g of the desired product. M.P. 125°–127° C.

EXAMPLE 36e

6-[[[(1-,1-Dimethylethoxy)carbonyl]amino]methyl]-1,4-dihydro-5-hydroxy-4-oxo-2-pyridinecarboxylic acid, 1-methylhydrazide To a solution of the compound of Example 36d (1.49 g. 2.37 mmol) in 30 ml dimethylformamide 0.7 g 10% palladium on carbon catalyst were added and a stream of hydrogen was bubbled through the mixture for 1 hour. The catalyst was filtered off and the filtrate evaporated in vacuo. Trituration of the residue with ether yielded 0.61 g of the desired product. M.P. 188°–190° C. (dec.)

EXAMPLE 36f

6-[[[(1,1-Dimethylethoxy)carbonyl]amino]methyl]-1,4-dihydro-5-hydroxy-4-oxo-2-pyridinecarboxylic acid,[2R-[2α,3α(Z)]]-2-[2-[[[1-(2-amino-4-thiazolyl)-2-[(2-methyl-4-oxo-1-sulfo-3-azetidinyl)amino]-2-oxo-ethylidene To a solution of [2R-2α,3α(Z)]]-3-[[(2-amino-4-thiazolyl)-[(1-carboxy-1-methylethoxy)imino]acetyl]amino]-2-methyl-4-oxo-1-azetidinesulfonic acid, potassium salt (0.79 g. 1.82 mmol) in 20 ml N,N-dimethylformamide were added tributylamine (0.34 g. 1.82 mmol), N-hydroxybenzotriazole (0.25 g. 1.82 mmol), 4-dimethylaminopyridine (0.022 g. 0.182 mmol) and finally N'N-dicyclohexylcarbodiimide (0.42 g. 2.0 mmol). After stirring for 1 hour at room temperature the compound from Example 36E (0.57g. 1.82 mmol) was added and the mixture was stirred overnight. Another 0.1 molequ. N'N-dicyclohexylcarbodiimide were added and after stirring overnight the dicyclohexylurea was filtered off and the filtrate was evaporated in vacuo to give an oil. The oil was dissolved in 20 ml acetone and a solution of 0.616 g perfluorobutan sulfonic acid potassium salt in 5 ml acetone was added. The resulting crystals were filtered off and dried in vacuo. Yield 1.16 g (83%) crude product. 1.1 g were dissolved in 15 ml water acetonitrile 9:1 as eluents. The sample containing fractions (water:acetonitrile) were freeze dried to give 270 mg (19.3% of the title compound.

EXAMPLE 36g

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid 2-[[6-(aminomethyl)-1,4-dihydro-5-hydroxy-4-oxo-2-pyridinylcarbonyl]-2-methylhydrazide To a suspension of the compound of Example 36f (255 mg. 0.33 mmol) in 0.3 anisole were added ml trifluoroacetic acid at 0° C. After stirring for 1 hour ether was added and the resulting precipitate was filtered off, washed with water and dried in vacuo. Yield 0.28 g (91%). M.P. 35°–255° C.

EXAMPLE 37

[2R-[2α,3α(Z)]]-[[[1-(2-Amino-4-thiazolyl)-2-[(2-methyl-4-oxo-1-sulfo-3-azetidinyl)amino]-2-oxoethylidene]amino]oxy]acetic acid, 2-[[6-aminomethyl)-1,4-dihydro-5-hydroxy-4-oxo-2-pyridinyl)carbonyl]-2-methylhydrazide, trifluoroacetate (1:2) salt

EXAMPLE 37a

1-[1,3-Dihydro-1,3-dioxo-2H-isoindol-zyl)oxy]acetic acid-2-methylhydrazide

To a solution of [(1,3-Dihydro-1,3-dioxo-2H-isoindol-2yl)oxy]acetyl chloride (5.99 g. 25.0 mmol) and 6 mg dimethylaminopyridine in 50 ml tetrahydrofuran, prepared at −5° C. to 0°, was added dropwise at 0° C. a solution of the compound of Example 36a (3.65 g. 25.0 mmol) and triethylamine (3.45 g. 34.1 mmol) in 25 ml tetrahydrofuran. After stirring overnight at 0° C., the precipitated salts were filtered off and the filtrate evaporated in vacuo. The residue was dissolved in 100 ml ethylacetate which was washed with 0.5 N hydrochloric acid, saturated sodium bicarbonate solution and subsequently with water. After drying and evaporation the desired product was obtained as a yellow, gummy foam. Yield 7.6 g (87%).

EXAMPLE 37b (Aminooxy)acetic acid, 2-[(1,1-dimethylethoxy)carbonyl-2-methyl hydrazide To a solution of the compound of Example 37a (7.46 g. 21.35 mmol) in 70 ml dichloromethane hydrazine hydrate (2.14 g. 42.71 mmol) was added slowly at 0° C. After stirring for 1.5 hours the precipitate was removed by filtration and the filtrate evaporated to yield the desired product as an oil. Yield 4.36 g.

EXAMPLE 37c (Z)-2-Amino-α-[[2-[2-[(1,1-dimethylethoxy) carbonyl]-2-methylhydrazino]-2-oxoethoxy]imino[-4-thiazoleacetic acid To a suspension of 2-amino-a-oxo-4-thiazoleacetic acid (3.22 g. 18.7 mmol) in 50 ml dimethylformamide of the compound of Example 37b (4.10 g. 18.7 mmol) was added. After 10 minutes a clear solution was obtained. The mixture was stirred for 2 days at room temperature. Evaporation and trituration of the residue with ether furnished 6.82 g (97.7%) of the title compound. M.P. >100° C. dec.

EXAMPLE 37d

2R-[2α,3α(Z)]]-[[[1-(2-Amino-4-thiazolyl)-2-[(2-methyl-4-oxo-1-sulfo-3-azetidinyl)amino-2-oxoethylidene(amino]oxy]acetic acid. 2-[(1,1-dimethylethoxy)carbonyl]-2-methylhydrazide, monopotassium salt To a solution of the compound of Example 37c (6.66 g, 17.83 mmol) in 180 ml dimethylformamide were added hydroxybenzotriazole (2.41 g, 17.83 mmol), dimethylaminopyridine (0.22 g, 1.78 mmol) and dicyclohexylcarbodiimide (4.05 g, 19.62 mmol). After stirring for 30 minutes a prestirred (30 minutes) solution of (2R-cis)-3-amino-2-methyl-4-oxo-1-azetidine-sulfonic acid, (3.21 g, 17.83 mmol) and tributylamine (3.31 g, 17.83 mmol) in 45 ml dimethylformamide was added. After stirring overnight, the precipitated dicyclohexylurea was filtered off and the solvent distilled off in vacuo. The residue was taken up in acetone and perfluorobutane sulfonic acid potassium salt (6.63 g, 19.6 mmol) were added. After addition of an equal volume of ether the precipitated salt was filtered and dried in vacuo. Yield 9.68 g (94.6%). M.P.>240° C. dec.

EXAMPLE 37e

[2R-[2α,3α(Z)]]-[[[1-(2-Amino-4-thiazolyl)-2-[(2-methyl-4-oxo-1-sulfo-3-azetidinyl)amino]-2-oxoethylidene]amino]oxy]acetic acid. 2-methylhydrazide, monosodium salt To a suspension of the compound of example 37d (9.68 g, 16.87 mmol) in 10 ml anisole were slowly added at 0° C. 100 ml trifluoro acetic acid. After stirring for 1 hour at 0° C. 750 ml ether were added. The resulting crystalline solid was collected by filtration, washed with ether and dried in vacuo; 10.83 g trifluoroacetic acid salt of the title compound. This salt was dissolved in water, the pH was brought to 6.5 with 3N NaOH aqueous solution and the solution chromatographed on HP 20 with water and water:acetonitrile 9:1 as eluent. Yield 3.32 g.

EXAMPLE 37f

6-[[[(1,1-Dimethylethoxy)carbonylamino]-methyl]-1,4-dihydro-5-hydroxy-4-oxo-2-pyridinecarboxylic acid. [2R-[2α,3α(Z)]]-2-[[[[1-(2-amino-4-thiazolyl)-2-[(2-methyl-4-oxo-1-sulfo-3-azetidinyl(amino]-2-oxoethylidene]amino]oxy]acetyl]-1-methylhydrazide, monopotassium salt To a solution of the compound of Example 28a (0.85 g, 3.0 mmol) in 50 ml dimethylformamide were added N-hydroxybenzotriazole (0.48 g, 3.0 mmol), dimethylamino pyridine (36 mg, 0.3 mmol) and dicyclohexylcarbodiimide (0.68 g, 3.0 mmol) After stirring for four hours a solution of the compound of Example 37e (1.24 g, 2.7 mmol) in 10 ml N,N'dimethylformamide was added dropwise. After stirring overnight the mixture was concentrated and the dicyclohexylurea was filtered off. The filtrate was evaporated and the residue triturated with 50 ml acetone. After filtration the filtrate was concentrated to 25 ml and 1.21 g perfluorobutan sulfonic acid potassium salt were added. After addition of 200 ml ether the resulting precipitate was filtered off and dried. Yield 1.70 g crude material. The crude compound was dissolved in water and chromatographed on XAD with water and a water acetonitrile gradient (till 3). The sample containing fractions (8:2 acetonitrile) were freeze dried to give 140 mg (7.0%) of the desired compound with a purity of 96.2%.

The material which was insoluble in acetone was suspended in water and the pH was adjusted to 6.5 with 3N KOH. The resulting solution was chromatographed in the same way as described above to give 240 mg.

The combined yields were chromatographed on Organogen with a water:acetonitrile gradient to give the following fractions: 31 mg (HI =81.8%), 191 mg (purity=95.2%); 100 mg (purity=95.3%). M.P. >300° C.

EXAMPLE 37g

[2R-[2α,3α(Z)]]-[[[1-(2-Amino-4-thiazolyl)-2-[(2-methyl-4-oxo-1-sulfo-3-azetidinyl)amino]-2-oxoethylidene]aminooxy]acetic acid, 2-[[6-aminomethyl)-1,4-dihydro-5-hydroxy-4-oxo-2-pyridinyl)carbonyl]-2-methylhydradie, trifluoroacetate (1:2) salt To a suspension of the compound of Example 37f (260 mg, 0.35 mmol) in 1.5 ml anisole were added dropwise at 0° C. 15 ml trifluoroacetic acid. After stirring for one hour at 0° C. ether was added and the resulting salt was filtered off, washed with ether and dried in vacuo. Yield: 220 mg. M.P.>190° C. (dec.)

EXAMPLE 38

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 1-methyl-2-[[6-(aminomethyl)-1,4-dihydro-5-hydroxy-2-pyridinyl]carbonyl]hydrazide, monopotassium salt, trifluoroacetate (1:1) salt

EXAMPLE 38a

1-Methylhydrazinecarboxylic acid phenylmethyl ester

To an ice cold, stirred solution of 36.8 (0.8 mol; 42.49 ml) methylhydrazine and 161.6 g (1.6 mol, 224 ml) triethylamine in 700 ml tetrahydrofuran were added dropwise 136.5 g (0.8 mol, 113.6 ml) benzylchloroformate. After stirring at room temperature overnight, the tetrahydrofuran was evaporated and the residue was worked up with ethylacetate/water (pH=9.0. Insoluble material was removed by filtration and the organic phase was washed (H₂O), dried (MgSO₄) and evaporated. The oily residue was stirred with 1 l. of ether, the etherial solution was decanted from insoluble material and evaporated to give 61 g of an oil which was dissolved in 200 ml MeOH containing 25 ml conc. HCl. After evaporation to dryness, the residue was recrystallized from EtOH/ ethylacetate to give 22.0 g of the hydrochloride of 2 as colorless crystals. This material was dissolved in water and the pH was adjusted to 9.0. Extraction with ethylacetate, drying of the organic phase (MgSO₄) and evaporation yielded 19.0 g of the title compound as a colorless oil.

EXAMPLE 38b

1-Methyl-1,2-hydrazinedicarboxylic acid, 2-(1,1-dimethylethyl)-1-(phenylmethyl) ester 15.80 g (87 mmol) of the compound of Example 38a, 24.00 g (110 mmol) (BOC)₂O and 10 mg 4-dimethylaminopyridine were heated in 80 ml acetonitrile/water (1:1) for 48 hours at 60° C. The solvents were evaporated, and the residue was dissolved in ethylacetate. After washing with 0.1 m citric acid solution, drying (MgSO₄) and evaporation 20.0 g crude title compound were obtained which was chromatographed on silica with ethylacetate/cyclohexane (1:1) to give 15.0 g (61%) pure title compound as a colorless solid. m.p. 60°–65° C.

EXAMPLE 38c

2-Methylhydrazinecarboxylic acid, 1,1-dimethylethyl ester 15.0 g (53 mmol) of the compound of Example 38b were hydrogenated in 100 ml MeOH containing 4.9 ml conc. HCl in the presence of 3.0 g palladium/carbon (10%) for 60 minutes. The ethylacetatecyclohexane, detection with phosphorous molybdic acid spray showed complete conversion. After filtration through celite, the solvent was evaporated and the residue was dissolved in water. Adjustment of the pH to 8.0 and extraction with ethylacetate yielded 5.6 g pure title compound. M.P. 50° C.

EXAMPLE 38d

2-[1,3-Dihydro-1,3-dioxo-2H-isoindol-2-yl)-oxy]-2-methylpropanoic acid,
2,-[(1,1-dimethylethoxy)carbonyl]-1-methylhydrazide 5.3 g (0.022 mol) of phthylimidoisobutyric acidchloride were dissolve in 40 ml dry tetrahydrofuran, and 4.10 ml (0.03 mol) triethylamine containing 5 mg 4-dimethylaminopyridine were added. A solution of 2.90 g (0.02 mol) of the compound of Example 38c in 20.0 ml tetrahydrofuran was then added dropwise at 0° C. The mixture was stirred overnight at room temperature and the solvent evaporated. The remaining solid was worked up with ethylacetate/water. The organic phase was washed (0.5 N-HCl, bicarbonate, water), dried (MgSO₄) and evaporated to give 6.6 g (88%) of a solid, m.p. 140°–145° C.

EXAMPLE 38e (Aminooxy)acetic acid,
2-[(1,1-dimethylethoxy)carbonyl]-1-methylhydrazide 7.10 g (0.019 mol) of the compound of Example 38d were dissolved in 50.0 ml methylchloride and 1.80 ml (0.038 mol) hydrazinehydrate were added dropwise at 0° C. with stirring upon which a precipitate was formed. After 30 minutes the solid was filtered off (3.5 g) and the filtrate was evaporated to give an amorphous residue (4.7 g) which was crystallized from ether/petroleumether to give 3.8 g as a colorless solid. M.P. 85°–90° C.

EXAMPLE 38f (Z)-2-Amino-α-[[2-[2-[(1,1-dimethylethoxy)carbonyl]-1-methylhydrazino]-1,1-dimethyl-2-oxoethoxy]imino]-4-thiazoleacetic acid 1.72 g (0.01 mol) Insert 3,4-Bis(phenylmethoxy)-2-pyridinemethanol, acetate ester were dissolved with rapid magnetic stirring in 25 ml dimethylformamide. To this solution was added a solution of 2.47 g (0.01 mmol of the compound of Example 38e in 10 ml dimethylformamde. After stirring at room temperature overnight, the dimethylformamide was evaporated in vacuo and the oil residue (6.0 g) was treated with ether upon which crystallization occurred. The yellowish crystals were filtered off and dried to give 3.3 g of the title compound, m.p. 145° C.

EXAMPLE 38g

[2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy]-2-methylpropanoic acid,
1-methyl-2-[(1,1-dimethylethoxy)carbonyl]hydrazide,
monopotassium salt Two solutions were prepared: a) 2.00 g (0.005 mol) of the compound of Example 38f were dissolved in 40 ml dimethylformamide. The mixture was cooled with ice and 0.76 g (0.005 mol) hydroxybenzotriazole (13% water) followed by 1.23 g (0.006 mol) dicyclohexylcarbodiimide were added. After 10 minutes dicyclohexylurea precipitated. b) 0.83 g (0.005 mol) (2R-cis)-3-amino-2-methyl-4-oxo-1-azetidine-sulfonic acid, were dissolved in 20 ml dimethylformamide containing 0.70 ml (0.005 mol) triethylamine. Solution b) was added dropwise to solution a) at 0°–5° C. The mixture was allowed to warm up to room temperature and was stirred overnight. The dicyclohexylurea was filtered off and the dimethylformamide was evaporated. The resulting oily residue was dissolved in acetone, filtered (traces of dicyclohexylurea was removed), and the acetonesolution was treated with 1.9 g (0.0055 mol) perfluorobutanesulfonic acid potassium salt. (Some white precipitate formed). Ether was added until no more precipitation occurred. A white solid was obtained by filtration and drying (2.61 g) which was dissolved in water and chromatographed on Organogen with water, 10% acetonitrile, product containing fractions (tlc-solvent acetonitrile/0.1 N-phosphate-buffer ph 5/CH₃CO₂H 3:6:1 on Merck RP-plates) were pooled and freeze dried to yield 1.4 g of the title compound. M.P. 210°–240° C.

EXAMPLE 38h

[2R-[2α,3α(Z)]]-2-[[[1-(2-Amino-4-thiazolyl)-2-[(2-methyl-4-oxo
-1-sulfo-3-azetidinyl)amino]-2-oxoethylidene]amino]oxy-2-methylpropanoic acid,
1,-methylhydrazide 1.1 g of compound of Example 38 g was stirred at 0°–5° C. with 45 ml trifluoroacetic acid for 3 hours. After evaporation the resulting oily reside was treated with ether resulting in colorless crystals of the title compound. 1.34 g M.P. −225° C.

EXAMPLE 38I

6-[[[(1,1-Dimethylethoxy)carbonyl]amino]methyl]-1,4-dihydro-5-hydroxy-4-oxo-2-pyridinecarboxylic acid,
[2R-[2α,3α(Z)]]-2-[2-[[[1-2-amino-4-thiazolyl)-2-[(2-methyl
-4-oxo-1-sulfo-3-azetidinyl]amino]-2-oxo-ethylidene]amino]oxy]-2-methyl-1-oxopropyl]-2-methylhydrazide, monopotassium salt 0.85 g (3.0 mmol) 6-[[[(1-,1-Dimethylethoxy)carbonyl]amino]methyl]-1,4-dihydro-5-hydroxy-4-oxo-2-pyridinecarboxylic acid were dissolved in 50 ml dimethylformamide. To the clear solution 0.46 g hydroxybenzotriazole (containing 13% water) and 0.62 g dicyclohexylcarbodiimide were added and the mixture was stirred for 4 hours at room temperature. After the addition of 2.34 ml (5.4 mmol) trioctylamine a solution of 2.0 g (2.7 mmol) of the compound of Example 38h in 10 ml dimethylformamide was added dropwise. The mixture was stirred overnight at room temperature and filtered. The filtrate was evaporated in vacuo and the residue was taken up with acetone (50 ml) and filtered. The filtrate was evaporated to a volume of ca. 25 ml and 1.2 g of perfluorobutanesulfonic acid potassium salt in acetone were added as well as ca. 120 ml ether upon which a precipitate formed with was collected and dried.

EXAMPLE 38j

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 1-methyl-2-[[6-(aminomethyl)-1,4-dihydro-5-hydroxy-2-pyridinyl]carbonyl]hydrazide, monopotassium salt, trifluoroacetate (1:1) salt The compound from Example 38I was suspended in 5 ml methylchloride and cooled to 0° C. 20 ml trifluoroacetic acid was added dropwise and the mixture was stirred for another 30 minutes. At −5° C. 100 ml ether were added dropwise and the precipitate formed (200 mg) was collected. 170 mg of this material was triturated twice with isopropanol and cooled with ice. From the mother liquors of the isopropanol treatment 30 mg (HI=96.9) were precipitated with ether. (The absolute contents of this material was about 20% lower, as determined by HPLC.) The remaining solid was filtered off to give 63 mg of the title compound. M. P.=290° C. (dec)

What is claimed is:
1. Compounds of the formula

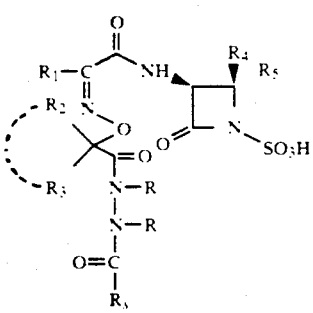

I and pharmaceutically acceptable salts thereof wherein:
$R_4$ and $R_5$ are the same or different and each is hydrogen, alkyl, alkenyl, alkynyl, cycloalkyl, phenyl, substituted phenyl or a 4, 5, 6 or 7-membered heterocycle or one of $R_4$ and $R_5$ is hydrogen and the other is azido, halomethyl, dihalomethyl, trihalomethyl, alkoxycarbonyl, 2-phenylethenyl, 2-phenylethynyl, carboxyl, —CH$_2$X$_1$, —S—X$_2$ or —O—X$_2$, $X_1$ is azido, amino, hydroxy, carboxyl, alkoxycarbonyl, alkanoylamino, phenylcarbonylamino, (substituted phenyl)carbonylamino, alkylsulfonyloxy, phenyl-sulfonyloxy, (substituted phenyl)sulfonyloxy, phenyl, substituted phenyl, $$\text{cyano-A}-\overset{\overset{O}{\|}}{C}-NX_6X_7.$$

—S—X$_2$, or —O—X$_2$ (wherein A, X$_2$, X$_6$ and X$_7$ are as hereinafter defined);

X$_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl, and in the case of when X$_1$ is O—X$_2$ then X$_2$ can also be alkylideneamino, alkanoylamino, carboxyalkylideneamino, alkylsulphonylamino, alkoxycarbonylalkylsulphonylamino or N,N-cyclodialkanoylamino, $$-O-\overset{\overset{X_3}{|}}{\underset{\underset{X_5}{|}}{C}}-X_4 \text{ or } -S-\overset{\overset{X_3}{|}}{\underset{\underset{X_5}{|}}{C}}-X-_4. \text{ or } -A-\overset{\overset{O}{\|}}{C}-NX_6X_7;$$

one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl (substituted amino)carbonyl, or cyano (—C≡N).

A is —CH=CH—, —(CH$_2$)$_m$—, —(CH$_2$)$_m$—O—, —(CH$_2$)$_m$—NH—, or —CH$_2$—S—CH$_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

$R_2$ and $R_3$ are the same or different and each is hydrogen or alkyl or $R_2$ and $R_3$ together with the carbon atom to which they are attached are a 3,4,5 or 6-membered cycloalkyl group R is hydrogen or methyl;

$R_5$ is a substituted hydroxy pyridone of the formulae:

II

III $R_1$ is phenyl, substituted phenyl, a 5 or 6-membered heterocycle containing one or two nitrogen, oxygen or sulfur atoms, substituted heterocycle;

$Y_1$ is CH$_2$X; COOR$_6$; CONR$_7$R$_8$; OH; OCH$_2$R$_9$; CHF$_2$; CHO; CH=N—OR$_{10}$; CH=CH—R$_{11}$; CN; CH=N—NHR$_{12}$;

X is hydrogen; halogen; OR$_{13}$; SR$_{14}$; SO$_2$R$_{15}$ NHR$_{16}$; NR$_{17}$ R$_{18}$; N$_3$; CN; SCH; COOR$_{19}$ CONH$_2$; CSNH$_2$; CH$_2$R$_{20}$;

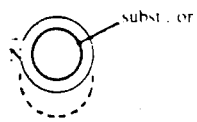

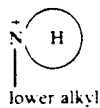

- $R_6$ is hydrogen; ion⁻; lower alkyl; substituted lower alkyl; aralkyl;
- $R_7$ and $R_8$ is hydrogen; one of $R_7$ and $R_8$ is hydrogen and the other lower alkyl; substituted lower alkyl; aralkyl; aryl or a 5 or 6 membered heterocycle; $R_7$ and $R_8$ may also be both lower alkyl or together form a saturated heterocycle;
- $R_9$ is hydrogen; lower alkyl; aryl; COOH; COO-lower alkyl; $CONH_2$;
- $R_{10}$ is hydrogen or lower alkyl
- $R_{11}$ is hydrogen; CN; COOH; COO-lower alkyl; O-lower alkyl; S-lower alkyl; halogen;
- $R_{12}$ is hydrogen; lower alkyl; CO-lower alkyl; aryl; heterocycle; CO-aryl or CO-heterocycle;
- $R_{13}$ is hydrogen; lower alkyl; $CH_2$—COO lower alkyl; $CH_2COOH$; $CONH_2$; $CH_2$—$CONH_2$;

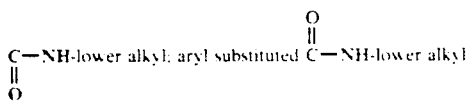

substituted aryl; CO-lower alkyl; CO-substituted lower alkyl; CO-aryl; CO-substituted aryl;
- $R_{14}$ is hydrogen; lower alkyl; —$CH_2COO$-lower alkyl; $CH_2COOH$; CH $CONH_2$; heterocycle; substituted heterocycle;
- $R_{15}$ is hydrogen; lower alkyl; $CH_2COO$-lower alkyl; $CH_2COOH$; $CH_2CONH_2$;
- $R_{16}$ is hydrogen; lower alkyl; $CONH_2$; CONH-lower alkyl; CONH-aryl; CONH substituted lower alkyl; CH=NH

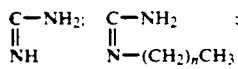

$CSNH_2$; CSNH lower alkyl; CSNH aryl; CSNH-heterocycle; n−1−3; $CH_2$—COOH; $CH_2$—COO-lower alkyl; $CH_2CH_2NH_2$; $CH_2$—$CH_2NH$—CO lower alkyl;
- $R_{17}$ and $R_{18}$ is hydrogen and the other lower alkyl or together form a saturated heterocycle;
- $R_{19}$ is hydrogen; lower alkyl;
- $R_{20}$ is hydrogen; COOH; COO lower alkyl; CN; OH;
- $Y_2$ is hydrogen; COOH, $CONH_2$; CN; $CSNH_2$; COO lower alkyl; $CONR_7R_8$;

wherein the term "substituted alkyl" refers to alkyl groups substituted with azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the term "substituted alkanoyl" refers to alkyl groups substituted with azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl, or carboxy groups;

the term "a 4,5,6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl groups has 1 to 4 carbon atoms;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl or one of the above groups substituted with one or more oxo, halogen, hydroxy, nitro, amino, cyano, trifluoromethyl, alkyl (of 1 to 4 carbon atoms), alkoxy (of 1 to 4 carbon atoms), alkylsulfonyl, phenyl, substituted phenyl, 2furfurylideneamino, benzylideneamino, or substituted alkyl wherein the alkyl group has 1 to 4 carbon atoms;

the term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino.

2. A compound according to claim 1 wherein $R_5$ is

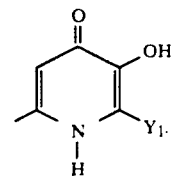

3. A compound according to claim 1 wherein $R_5$ is

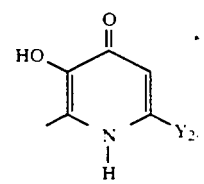

4. A compound according to claim 2 wherein $Y_1$ is $CH_2X$.

5. A compound according to claim 4 wherein X is hydrogen.

6. A compound according to claim 2 wherein $Y_1$ is $COOR_6$.

7. A compound according to claim 2 wherein $Y_1$ is $CONR_7R_8$.

8. A compound according to claim 2 wherein $Y_1$ is OH.

9. A compound according to claim 2 wherein $Y_1$ is $OCH_2R_9$.

10. A compound according to claim 2 wherein $Y_1$ is $CHF_2$.

11. A compound according to claim 2 wherein $Y_1$ is CHO.

12. A compound according to claim 2 wherein $Y_1$ is $CH=N-OR_{10}$.

13. A compound according to claim 2 wherein $Y_1$ is $CH=CH-R_{11}$.

14. A compound according to claim 2 wherein $Y_1$ is CN.

15. A compound according to claim 2 wherein $Y_1$ is $CH_2N-NHR_{12}$.

16. A compound according to claim 3 wherein $Y_2$ is hydrogen.

17. A compound according to claim 3 wherein $Y_2$ is COOH.

18. A compound according to claim 3 wherein $Y_2$ is $CONH_2$.

19. A compound according to claim 3 wherein $Y_2$ is CN.

20. A compound according to claim 3 wherein $Y_2$ is $CSNH_2$.

21. A compound according to claim 3 wherein $Y_2$ is COO-lower alkyl.

22. A compound according to claim 3 wherein $Y_2$ is $CONR_7R_8$.

23. A compound according to claim 1, 2S-2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[[1,4-dihydro-5-hydroxy-6-(hydroxymethyl)-4-oxo2-pyridinyl]carbonyl]hydrazide, monopotassium salt.

24. A compound according to claim 1, 2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(1,4-dihydro-5-hydroxy-6-methoxy-4-oxo-2-pyridinyl)carbonyl]hydrazide,monopotassium salt.

25. A compound according to claim 1, [2S-[2α,3β(Z)]]-2-[[[1-(2-Amino-4-thiazolyl-2-(2-methyl-4-oxo-1-sulfo-3-azetidinyl)amino]-2-oxoethylidene]amino]oxy]-2-methylpropanoic acid, 2-[(1,4-dihydro-3-hydroxy-4-oxo-2-pyridinyl)carbonyl]hydrazide, monopotassium salt.

26. A compound according to claim 1, [2R-[2α,3α(Z)]]-2-[[[1-(2-Amino-4-thiazolyl)2-[(2-methyl-4-oxo-1-sulfo-3-azetidinyl)amino]-2-oxoethylidene]amino]oxy]-2-methylpropanoic acid, 2-[[1,4-dihydro-5-hydroxy-6-(pyridinomethyl)-2-pyridinyl]carbonyl]hydrazide, inner salt.

27. A compound according to claim 1, 2R-[2α,3α(Z)]]-2-[[[1-(2-Amino-4-thiazolyl)-2-(2-methyl-4-oxo-1-sulfo-3-azetidinyl)amino]-2-oxoethylidene]amino]oxy]-2-methylpropanoic acid, 2-[6-(aminomethyl)-1,4-dihydro-5-hydroxy-4-oxo-2-pyridinyl]carbonyl]hydrazide, trifluoroacetate (1:1) salt.

28. A compound according to claim 1, [2R-2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid; 2-[[1,4-dihydro-5-hydroxy-6-[(1-methyl-1-pyrrolidinyl)methyl]-4-oxo-2-pyridinyl]carbonyl]hydrazide, inner salt.

29. A compound according to claim 1, (2R-cis)-1,4-Dihydro-3-hydroxy-4-oxo-2,6-pyridinedicarboxylic acid, 2-[2-[[[1-(2-amino-4-thiozolyl)-2-[(2-methyl-4-oxo-1-sulfo-3-azetidinyl)amino]-2-oxoethylidene]amino]oxy]-2-methyl-1-oxopropyl]hydrazide, dipotassium salt.

30. A compound according to claim 1, [2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[[6-(aminocarbonyl)-1,4-dihydro-5-hydroxy-4-oxo2-pyridinyl]carbonyl]hydrazide,monopotassium salt.

31. A compound according to claim 1, 2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid. 2-[(1,4-dihydro-6-cyano-5-hydroxy-4-oxo-2-pyridinyl)carbonyl]hydrazide, monopotassium salt.

32. A compound according to claim 1, [2R-[2α,3α(Z)]]-2-[[[1-(2-methyl-4-oxo-1-sulfo-3-azetidinyl)amino]-2-oxoethylidene]amino]oxy]-2-methylpropanoic acid, 2-[[6-[[(aminocarbonyl)amino]methyl]-1,4-dihydro-5-hydroxy-4-oxo-2-pyridinyl]carbonyl]

33. A compound according to claim 1, [2R-2α,3β(Z)]]-2-[[[1-(2-Amino-4-thiazolyl)-2[-(2-methyl-4-oxo-1-sulfo-3-azetidinyl)amino]-2-oxoethylidene]amino]oxy]-2-methylpropanoic acid,2-[(6-carboxy-1,4-dihydro-5-hydroxy-4-oxo-2-pyridinyl)carbonyl]hydrazide-4-potassium salt.

34. A compound according to claim 1, 2R-[2α,3α(Z)]]-2-[[[1-(2-Amino-4-thiazolyl)-2-[(2-methyl-4-oxo-1-sulfo-3-azetidinyl)-amino]-2-oxoethylidene]amino]oxy]-2-methyl-propanoic acid, 2-[[1,4-dihydro-5-hydroxy-6-(1-methyl-4-pyridinio)thio]methyl]-2-pyridinyl]carbonyl]-hydrazide, inner salt.

35. A compound according to claim 1, 2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[[1,4-dihydro-5-hydroxy-6-(hydroxymethyl)-2-pyridinyl]carbonyl]hydrazide,monopotassium salt.

36. A compound according to claim 1, [2R-[2α,3α(Z)]]-1-[1-(2-Amino-4-thiazolyl)-2-(2-methyl-4-oxo-1-sulfo-3-azetidinyl)amino]-2-oxoethylidene]amino]oxy]cyclopentanecarboxylic acid, 2-[[1,4-dihydro-5-hydroxy-6-(hydroxymethyl)-4-oxo-2-pyridinyl]carbonyl]hydrazide, monopotassium salt.

37. A compound according to claim 1, [2R-[2α,3α(Z)]]-1-[[1-(2-Amino-4-thiazolyl)-2-[(2-methyl-4-oxo-1-sulfo-3-azetidinyl)-amino]-2-oxoethylidene]amino]oxy]cyclopentanecarboxylic acid, 2-[[6-(aminomethyl)1,4-dihydro5-hydroxy-4-oxo-2-pyridinyl)carbonyl]hydrazide, monopotassium salt trifluoroacetate (1:1) salt.

38. A compound according to claim 1, [2S-[2α,3α(Z)]]-1-[[1-(2-Amino-4-thiazolyl)-2-[(2-methyl-4-oxo-1-sulfo-3-azetidinyl)-amino]-2-oxoethylidene]amino]oxy]-2-methylpropanoic acid, 2-[[6-(aminomethyl)-1,4-dihydro-dihydro-5-hydroxy-4-oxo-2-pyridinyl]carbonyl]-hydrazide, monopotassium salt, trifluoroacetate (1:1) salt.

39. A compound according to claim 1, 2R-[α,3α(Z)]]-[[[1-(2-Amino-4-thiazolyl)-2-(2-methyl-4-oxo-1-sulfo-3-azetidinyl)-amino]-2-oxoethylidene]amino]oxy]acetic acid. 2-[(6-aminoethyl)-1,4-dihydro-5-hydroxy-4-oxo-2-pyridinyl)carbonyl]hydrazide, monopotassium salt,trifluoroacetate (1:1) salt.

40. A compound according to claim 1, [2-R-2α,-3α(Z,S)]]-2-[1-(2-Amino-4-thiazolyl)-2-[(2-methyl-4-oxo-1-sulfo-3-azetidinyl)amino]-2-oxo-ethylidene]amino]oxy]propanoic acid.2-[6-(aminomethyl)-1,4-dihydro-5-hydroxy-4-oxo-2-pyridinyl]carbonyl]hydrazide, trifluoroacetate (1:3) salt.

41. A compound according to claim 1, [2R-2α,-3α(Z,S)]]-2-[[1-(2-Amino-4-thiazolyl)-2-[(2-methyl-4-oxo-1-sulfo-3-azetidinyl)amino]-2-oxoethylidene]amino]oxy]propanoic acid.2-[[6-aminomethyl)-1,4-dihydro-5-hydroxy-4-oxo-2-pyridinyl]carbonyl]hydrazide.

42. A compound according to claim 1, [2R-[2α,3α(Z)]]-4-(Aminocarbonyl)-1-[6-[[2-[2-[[[1-(2-amino-4-thiazolyl)-2-[(2-methyl-4-oxo-1-sulfo-3-azetidinyl]amino2-oxoethylidene]-amino]oxy]-2-methyl-1-oxopropyl]hydrazino]carbonyl]1,4-dihydro-3-hydroxy-4-oxo-2-pyridinyl]]-methyl]pyridinium inner salt.

43. A compound according to claim 1, [2R-[2α,-3α(Z)]]-2-[[1-(2-Amino-4-thiazolyl)-2-[(2-methyl-4-oxo-1-sulfo-3-azetidinyl)-amino]-2-oxoethylidene]amino]oxy]-2-methylpropanoic acid 2-[6-(aminomethyl)-1,4-dihydro-5-hydroxy-4-oxo-2-pyridinylcarbonyl]-2-methyl-hydrazide.

44. A compound according to claim 1, [2R-[2α,-3α(Z)]]-[[[1-(2-Amino-4-thiazolyl)-2-[(2-methyl-4-oxo-1-sulfo-3-azetidinyl)amino]-2-oxoethylidene]amino]oxy]acetic acid, 2[[6-aminomethyl)-1,4-dihydro-5-hydroxy-4-oxo-2-pyridinyl)carbonyl]-2-methylhydradie, trifluoroacetate (1:2) salt.

45. A compound according to claim 1, [2R-[2α,-3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 1-methyl-2-[[6-(aminomethyl)-1,4-dihydro-5-hydroxy-2-pyridinyl]carbonyl]hydrazide, monopotassium salt, trifluoroacetate (1:1) salt.

* * * * *

UNITED STATES PATENT AND TRADEMARK OFFICE
CERTIFICATE OF CORRECTION

PATENT NO. : 5,112,968
DATED : May 12, 1992
INVENTOR(S) : Uwe D. Treuner

It is certified that error appears in the above-identified patent and that said Letters Patent is hereby corrected as shown below:

In Claim 1, column 49, lines 61-65, the word "cyano" should be placed after the words "substituted phenyl," on line 61.

In Claim 1, column 50, line 38, after the word "group", insert --;--.

In Claim 1, column 51, line 26, after the word "alkyl", insert --;--.

In Claim 1, column 51, line 48, after the formula "CH=NH", insert --;--.

In Claim 1, column 51, line 55, after the letter "n", delete the hyphen and insert the symbol --=-- in its place.

In Claim 26, column 53, line 60, after the word "-hydroxy-", insert -- 4-oxo- --.

Signed and Sealed this

Tenth Day of August, 1993

Attest:

MICHAEL K. KIRK

Attesting Officer          Acting Commissioner of Patents and Trademarks